United States Patent
Parkins

(10) Patent No.: US 10,258,509 B2
(45) Date of Patent: Apr. 16, 2019

(54) IN-EAR NOISE DOSIMETRY SYSTEM

(71) Applicant: Red Tail Hawk Corporation, Philadelphia, PA (US)

(72) Inventor: John W. Parkins, Philadelphia, PA (US)

(73) Assignee: Red Tail Hawk Corporation, Philadelphia, PA (US)

( * ) Notice: Subject to any disclaimer, the term of this patent is extended or adjusted under 35 U.S.C. 154(b) by 0 days.

(21) Appl. No.: 15/497,970

(22) Filed: Apr. 26, 2017

(65) Prior Publication Data

US 2017/0312135 A1 Nov. 2, 2017

Related U.S. Application Data

(60) Provisional application No. 62/328,065, filed on Apr. 27, 2016, provisional application No. 62/409,930, filed on Oct. 19, 2016.

(51) Int. Cl.
*A61F 11/06* (2006.01)
*H04R 1/10* (2006.01)
(Continued)

(52) U.S. Cl.
CPC .............. *A61F 11/08* (2013.01); *A61B 5/01* (2013.01); *A61B 5/12* (2013.01); *A61B 5/6817* (2013.01);
(Continued)

(58) Field of Classification Search
CPC ......... A61F 11/08; A61B 5/12; H04R 1/1016; H04R 1/1041; H04R 1/1083;
(Continued)

(56) References Cited

U.S. PATENT DOCUMENTS 5,692,059 A 11/1997 Kruger
5,757,930 A 5/1998 Seidemann et al.
(Continued)

FOREIGN PATENT DOCUMENTS

WO 2012071650 A1 6/2012

OTHER PUBLICATIONS

International Search Report for PCT/US2017/057297 dated Jan. 29, 2018.
(Continued)

*Primary Examiner* — Xu Mei
(74) *Attorney, Agent, or Firm* — Brown & Michaels, PC

(57) ABSTRACT

An in-ear noise dosimeter in the form of an earplug which senses sound in the ear canal using an eartip which has a sound delivery channel that couples sound at the end closest to the eardrum to an earplug microphone. The earplug can communicate wirelessly with a remote data collection and processing system. A dock unit for storing the earplugs when not worn can compensate for differences in unoccluded-ear versus occluded-ear responses by an acoustic compensator. An electronic compensation filter can be modified by a proximity switch in the earplug which changes state when the earplug is worn in the ear versus stored in a dock unit. The dosimeter can also have a temperature sensor for sensing human body temperature and remotely-located wireless LEDs used to alert the user of high noise dosage. Data can also be downloaded from the earplug using a reader unit.

31 Claims, 13 Drawing Sheets

(51) Int. Cl.
  *A61F 11/08* (2006.01)
  *A61B 5/12* (2006.01)
  *A61B 5/01* (2006.01)
  *A61B 5/00* (2006.01)
  *H04R 3/02* (2006.01)
(52) U.S. Cl.
  CPC ......... *H04R 1/1016* (2013.01); *H04R 1/1041* (2013.01); *H04R 1/1083* (2013.01); *A61B 2560/0242* (2013.01); *A61B 2562/0204* (2013.01); *H04R 2420/07* (2013.01); *H04R 2460/15* (2013.01)
(58) Field of Classification Search
  CPC ............ H04R 2420/07; H04R 2460/01; G10K 11/175; G10K 11/17833; G10K 11/17837
  USPC .... 381/71.6, 72, 73.1, 74, 317, 328, 380, 63
  See application file for complete search history.

(56) References Cited

U.S. PATENT DOCUMENTS

| | | | |
|---|---|---|---|
| 5,970,795 A | 10/1999 | Seidmann et al. | |
| 6,456,199 B1 | 9/2002 | Michael | |
| 6,507,650 B1* | 1/2003 | Moquin | G01H 3/14 379/387.01 |
| 7,039,195 B1* | 5/2006 | Svean | A61F 11/08 381/71.1 |
| 7,289,636 B2* | 10/2007 | Saunders | A61F 11/08 381/317 |
| 7,688,983 B2 | 3/2010 | Voix et al. | |
| 7,978,861 B2 | 7/2011 | Michael | |
| 8,218,784 B2 | 7/2012 | Schulein et al. | |
| 8,391,503 B2* | 3/2013 | Bayley | G01H 3/14 381/309 |
| 8,737,630 B2* | 5/2014 | Chang | H04R 29/001 381/56 |
| 8,848,929 B2 | 9/2014 | Schiller et al. | |
| 2003/0191609 A1* | 10/2003 | Bernardi | G01H 3/14 702/191 |
| 2010/0141439 A1* | 6/2010 | Lunner | G01H 3/14 340/540 |
| 2010/0278350 A1 | 11/2010 | Rung | |
| 2013/0266152 A1* | 10/2013 | Haynie | H04R 5/033 381/80 |
| 2014/0177863 A1 | 6/2014 | Parkins | |
| 2014/0185816 A1 | 7/2014 | Kim et al. | |
| 2014/0294191 A1* | 10/2014 | Parkins | A61F 11/06 381/72 |
| 2015/0256010 A1* | 9/2015 | Scandurra | H02J 7/0044 320/107 |

OTHER PUBLICATIONS

"SL13A—Smart Sensory Tag Chip for Unique Identification, Monitoring and Data Logging", ams Datasheet; May 2014.
Series P: Telephone Transmission Quality—Objective measuring apparatus—Head and torso simulator for telephonometry, International Telecommunication Union; Aug. 1996.
"Sound pick-up free field frequency response of HATS", International Telecommunication Union; Aug. 1996.
American National Standard, "ANSI S1.42—Design Response of Weighting Networks for Acoustical Measurements", Accredited Standards Committee S1, Acoustics; Apr. 2011.
American National Standard, "ANSI S1.25—Specification for Personal Noise Dosimeters", ccredited Standards Committee S1, Acoustics; 1991.
American National Standard, "ANSI S3.36—Specification for a Manikin for Simulated in-situ Airborne Acoustic Measurements", American Institute of Physics for the Acoustical Society of America; 2001.
Linear Technology, "LTC1967—Precision Extended Bandwidth, RMS-to-DC Converter"; 2011.

* cited by examiner

IN-EAR NOISE DOSIMETRY SYSTEM

REFERENCE TO RELATED APPLICATIONS

This application claims one or more inventions which were disclosed in Provisional Application No. 62/328,065, filed Apr. 27, 2016, entitled "In-Ear Noise Dosimetry System", and Provisional Application No. 62/409,930, filed Oct. 19, 2016, entitled "In-Ear Noise Dosimetry System". The benefit under 35 USC § 119(e) of the United States provisional applications is hereby claimed, and the aforementioned applications are hereby incorporated herein by reference.

ACKNOWLEDGMENT OF GOVERNMENT SUPPORT

This invention was made with government support under SBIR grant 1R43OH011145-01, awarded by the U.S. Centers for Disease Control and Prevention. The government has certain rights in the invention.

BACKGROUND OF THE INVENTION

Field of the Invention

The invention pertains to the field of measurement of sound levels. More particularly, the invention pertains to an in-ear noise dosimeter.

Description of Related Art

Hearing loss accounted for at least 14% of occupational illness in 2007, and approximately $242M is spent annually on worker's compensation for hearing loss disability. According to the CDC, four million workers go to work each day in damaging noise, while ten million in the U.S. suffer noise-related hearing loss. Approximately 82% of the occupational noise induced hearing loss (NIHL) was reported in the manufacturing sector. Occupational NIHL is an outsized problem considering our capability to virtually eliminate it.

Sound Pressure Level is measured in decibels (dB), and for the purposes of indicating the effect on human beings of sound pressure level in air, can be frequency-weighted to compensate for the sensitivity of the human ear. The most commonly used of such scales is "A" frequency weighting, so sound levels for occupational exposure are usually expressed in dBA units, meaning sound pressure in air measured in decibels and weighted by the "A" frequency weighting system. The decibel is a base-10 logarithmic unit, so that a difference of 6 dB indicates a doubling in sound pressure level, 20 dB indicates a factor of ten times, 40 dB an increase of 100 times, and so on. Thus, a sound level of 100 dBA is 10 times a sound level of 80 dBA, and what might appear to be a numerically small difference in dBA is actually a very large difference noise exposure. The standard for sound level meters is set out in ANSI specification S1.4, which is incorporated herein by reference.

The National Institute for Occupational Safety and Health (NIOSH), a part of the Centers for Disease Control (CDC), recommends that employees should not be exposed to sound at a level of 85 dBA for eight hours or more.

The OSHA Occupational Noise Exposure standard states that an employee must not receive sound at a time-weighted average (TWA) level of over 90 dBA of over an eight-hour period, and if an employee is exposed to 85 dB TWA, or above, over an eight-hour period, the employer shall administer a continuing, effective hearing conservation program. The standard also states that the employer shall establish and maintain an audiometric testing program by making audiometric testing available to all employees whose exposures equal or exceed an eight-hour TWA of 85 dB. Audiometric tests shall be conducted by a trained professional. If hearing thresholds shifts are measured in an employee, over time, hearing protectors and training of their use are required.

According to OSHA regulations, an employee may be exposed to 85 dBA TWA over a 16 hour period, compared to 90 dBA TWA for 8 hours. The change in decibels required for doubling the allowed exposure time is called the "exchange rate." For the OSHA regulation, the exchange rate is 5 dB.

Employees who are exposed to a TWA of 85 dB over eight hours, and do not have an audiogram baseline measurement, are required by the regulations to wear hearing protecting devices (HPDs) at no cost to the employee. Employers are required to provide training regarding use of the HPD and to ensure proper initial use.

Although, legally, employees may be exposed to 90 dBA for eight hours, a review of research by NIOSH shows that significant NIHL can occur at levels above 85 dBA for eight hours. NIOSH recommends a more restrictive maximum of 85 dB TWA exposure with a 3 dB exchange rate. Hence, even a 3 dB change in noise level is very significant.

Compliance with this standard is complicated and expensive regarding record retention, equipment and the involvement of professionals when a hearing conservation program is required.

In-ear personal noise dosimeters (iPNDs), like the one shown in prior art FIGS. 1 through 3, have been developed to address noise exposure in the workplace. The system in FIGS. 1 through 3 comprises in-ear dosimetry earplugs 2 (herein referred to as "earplugs" for brevity) that communicate with an electronics unit using electrical cables 4. As seen in FIG. 2, the earplugs 2 worn in an ear 11 have a microphone 6 within an earplug shell 8, and the shell is attached to an eartip 10. The earplug shell 8 is generally cylindrically shaped, in this example. The eartip 10 is also generally cylindrical in shape and has a sound delivery channel (SDC) 12 that allows sound in an ear canal 14 to be acoustically coupled from the ear canal 14 to the microphone 6. In this way, the microphone 6 can monitor the sound in the ear canal 14.

The eartip 10 and earplug shell 8 provide a barrier to the acoustic noise from the user's environment to reduce the noise exposure of the user. Eartips 10 may be constructed using foam, silicone, rubber or other materials that can form an acoustic seal with the walls of an ear canal 14, and can be custom fitting or universal fitting. Eartips 10 may be removable, as in the case with foam eartips, or permanently attached to the earplug shell 8, as is the case with custom-molded silicone earplugs, as known in the art.

The noise that reaches the ear canal 14, due to earplug 2 vibration and flanking acoustic transmission paths, is sensed by the earplug microphone 6. The microphone output is transmitted via electrical cables 4 to an electronics unit (not shown) that determines noise exposure, continuously. In this way, the user is protected from ambient noise in the environment, and the noise exposure of the user is monitored.

If the user needs to remove the earplugs 2, the electrical cables 4 may be draped behind the neck and over the shoulders so that the earplugs 2 lay on the chest, as seen in FIG. 3. The microphones 6 will then monitor the noise at the chest location, as an alternative for monitoring the noise at the center-head location, which is a preferred monitoring location.

In this way, if the user removes the earplugs 2 to talk to a co-worker during face-to-face communications, a higher noise exposure is measured by the electronics unit because the noise level at the unprotected chest location is higher than the noise level in a protected ear canal 14. The chest measurement is an alternative position compared to the measurement at the center head; however, the shoulder is a more common location to measure unprotected noise due to sound reflection from the chest and closer location of the shoulder to the head.

A problem with this technique of monitoring noise exposure in the ear canal 14, when the user is wearing the earplugs 2, as well as outside of the ear 11, when the user is not, is that the microphones 6 in the earplugs 2 are not measuring the correct acoustic transfer functions. The chest location is not as desirable as the shoulder location. Moreover, when the earplugs 2 are worn in the ear 11, the microphone 6 response should be compensated by the diffuse field response of the human ear, at least to some degree; otherwise, the in-ear measurements are too high and overestimate the exposure.

The noise dose measured assumes an unoccluded ear canal, which has a diffuse field response that significantly amplifies sound in the region of 2,000 Hz to 5,000 Hz due to acoustical resonances of the ear as seen in the ITU-T P.58 specification (Head and Torso Simulator For Telephonometry) table 3/P.58. A 14 dB boost can be seen at 2,500 Hz. When an iPND is used, the pressure measured in the ear canal is the actual pressure in the ear canal, assuming negligible occluded ear resonance.

This means that the iPND noise dose measurements are significantly too high. They should be compensated by the diffuse field response of the ear, by at least some degree, but are not, at this time. However, if they were compensated using an electrical filter, then when the earplugs were draped over the shoulder, the earplug microphone measurement would be incorrect because the microphone signal would be compensated by the in-ear compensation filter, but the earplugs would not be occluding the ear canal, and the filter shouldn't be used. That is, it would be beneficial to have two frequency responses for the system: one when the earplug is worn in the ear, and another when the earplug is not. Currently, iPNDs do not have this important feature.

Moreover, although wired iPNDs are effective, the wires connecting the earplugs to the dosimeter are problematic to many workers. The wires conduct vibration to the earplug causing earplug vibration and substantial sound generation. Moreover, when wired earplugs are used with earmuffs for double hearing protection, the wires create gaps that deteriorate attenuation provided by the earmuffs. Wires also tend to get caught on machinery or other objects causing a significant safety hazard. When moving the head, there is tugging on the earplugs that may cause an annoyance, and if wearing earmuffs over the earplugs, the wires put force on the earplugs also causing discomfort. Wires also reduce reliability, due to breakage, and the connectors needed are costly and can also fail. If the user is wearing hazardous materials headgear or other headgear that needs to create a gas-tight seal around the head, wires are also a problem as they break the gas-tight barrier.

SUMMARY OF THE INVENTION

The invention presents an in-ear noise dosimeter in the form of an earplug comprising an earplug shell, or body, that contains earplug components. An eartip, which has a sound delivery channel that acoustically couples sound at the proximal end of the eartip (closest to the eardrum when worn in an ear) to an earplug microphone, is attached to the earplug shell.

When the earplug is worn in a human ear, the microphone senses sound in the ear canal. The microphone communicates electrically with earplug electronics, located within the earplug. A battery, preferably rechargeable, is used in one embodiment to provide power for the earplug electronics and microphone. An earplug transceiver is used to communicate with a remote data collection and processing system.

In one wire-free embodiment, the earplug in this embodiment is free of external electrical cables and connectors. The earplug, in one embodiment, incorporates a switch that modifies the response of an audio signal derived from the microphone output depending on whether the earplug is in the ear or not in the ear. The invention also may make use of a temperature sensor for sensing human body temperature and remotely-located wireless light emitting diodes (LEDs) used to alert the user of high noise dosage.

The invention also presents a dock unit for storing the earplugs when not worn in the ear. In one embodiment of the invention, the dock unit compensates for differences in unoccluded-ear versus occluded-ear responses for measuring the unprotected and protected noise dose by incorporating an acoustic compensator.

The invention also presents a reader unit for downloading data from the earplug, charging an earplug battery and calibrating the earplug.

BRIEF DESCRIPTION OF THE DRAWING

FIG. 5b shows a top view of the earplug from FIG. 5a.

DETAILED DESCRIPTION OF THE INVENTION

The in-ear dosimetry system of the invention provides improved functionality and performance and addresses the problems of wires, the difference in occluded versus unoccluded ear responses, earplug storage and proper location of noise dose monitoring when the earplugs are not in the ears. The system also provides improved feedback to the user concerning overexposure, and monitors the health of the worker by monitoring body temperature, which is also used to determine if the user is wearing the earplugs.

Wires are eliminated using novel wireless techniques. Occluded ear responses are accounted for by using a novel electronic filter, so that the difference between occluded and unoccluded ear responses when the earplugs are worn and not worn is also addressed using novel electronic filters and acoustic compensation devices. A novel storage device for the earplugs creates a simple and sanitary storage solution that also functions to locate the earplugs in the correct location for noise monitoring when the earplugs are not worn.

The user does not need to remember to switch in electronic filtering using the current invention to account for unoccluded and occluded ear responses. The transfer functions are automatically modified to their correct responses just by storing the earplugs in a dock unit or by monitoring a temperature sensor that measures the temperature of the external ambient environment.

The dock unit is worn on the shoulder, in a preferred embodiment, providing the correct location for the noise dose measurement when the earplugs are not worn in the ear and the correct response is achieved at both the shoulder and in-ear locations using novel techniques.

Figure 4:
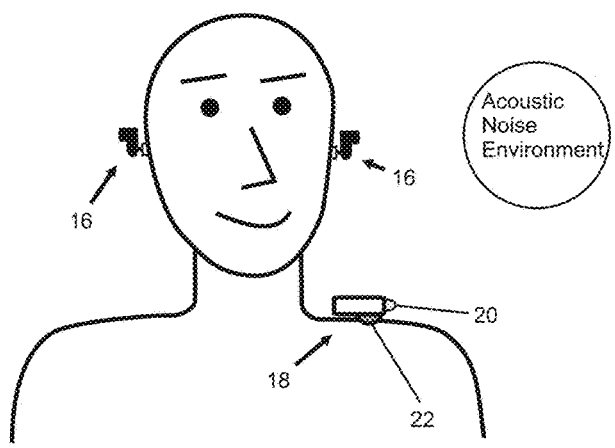
FIG. 4 shows an embodiment incorporating in-ear dosimetry earplugs and a dock unit.

A preferred embodiment of the system can be seen in FIG. 4. This embodiment incorporates wireless in-ear dosimetry earplugs 16 and a dock unit 18. The dock unit 18 comprises an ambient microphone 20, a vibration transducer 22 and associated dock unit electronics (not shown). These earplugs 16 can be worn effectively and comfortably under earmuffs, not shown, to achieve "double hearing protection."

Figure 5A:
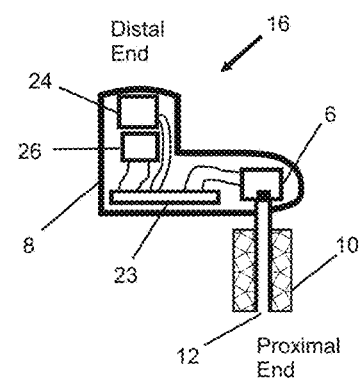
FIG. 5a shows a cross section of an embodiment of an in-ear dosimetry earplug.

A cross section of an embodiment of the in-ear dosimetry earplugs 16 of the current invention can be seen in FIG. 5a.

The earplugs comprise an earplug shell 8, or body, that contains earplug components. An eartip 10 is attached to the earplug shell 8 and has a sound delivery channel 12 that acoustically couples sound at the proximal end (closest to the eardrum when worn in an ear) of the eartip 10 to an earplug microphone 6.

Figure 2:
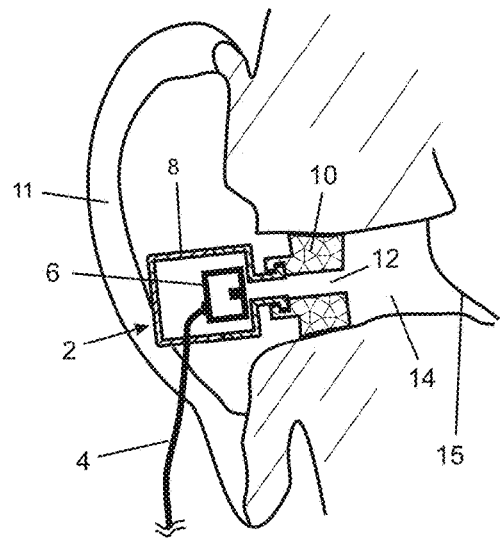
Figure 3:
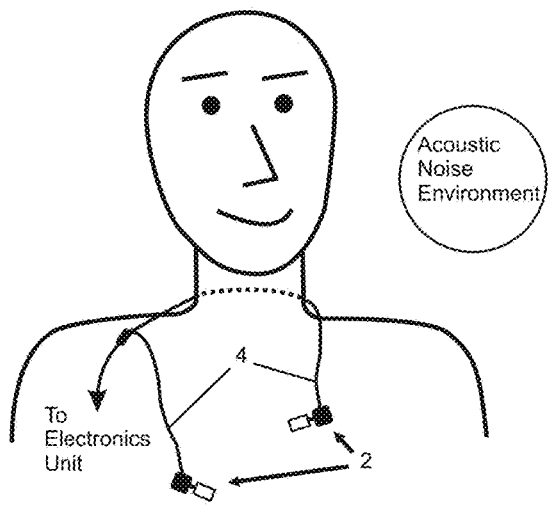

When the earplug 16 is worn in an ear 11, similar to how the earplug in FIG. 2 is worn in an ear 11, the microphone 6 senses sound in a human ear canal 14. The microphone 6 communicates electrically with earplug electronics 23, located within the earplug shell 8. A battery 24, preferably rechargeable, is used in this embodiment to provide power for the earplug electronics 23 and microphone 6.

Figure 5B:
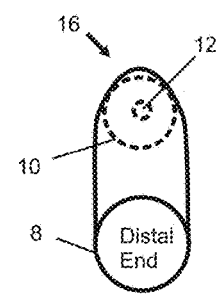

An earplug antenna 26 is used to communicate with a remote data collection and processing system (not shown). This wire-free embodiment eliminates the problems previously mentioned regarding wires. The earplug 16 in this embodiment is free of external electrical cables and connectors. A top view of the earplug 16 from FIG. 5a can be seen in FIG. 5b.

Figure 6:
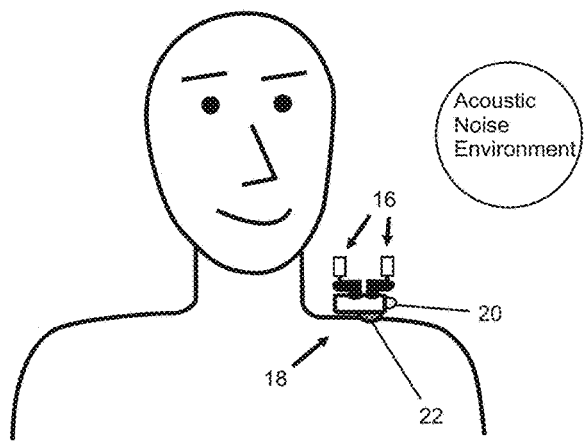
FIG. 6 shows how the earplugs can be stored in or on a dock unit.

In this embodiment, when the earplugs 16 are removed from the ears, they can be stored in or on a dock unit 18, as seen in FIG. 6. While the earplugs 16 are stored, they can continue to collect ambient noise data. The dock unit 18 has an ambient microphone 20 that can be used to collect ambient noise data. When the earplugs 16 are worn in the ear, time-stamped data collected by the earplugs 16 can be compared to time-stamped data collected by the dock unit 18 to determine actual noise attenuation provided by the earplugs 16. This information can be used to determine if a user wears his/her earplugs 16 properly. If the data indicate that a user is not wearing the earplugs 16 to achieve proper attenuation, a supervisor may intervene and work with the user to improve the earplug fit, preventing problems of hearing damage in the future.

A vibration transducer 22 in the dock unit can be used to provide tactile feedback to the user, such as when maximum noise dosage has been reached or if the earplugs 16 are not providing adequate protection, for example. The dock unit 18 of the current invention can be used with both wired and wireless iPNDs.

Figure 7:
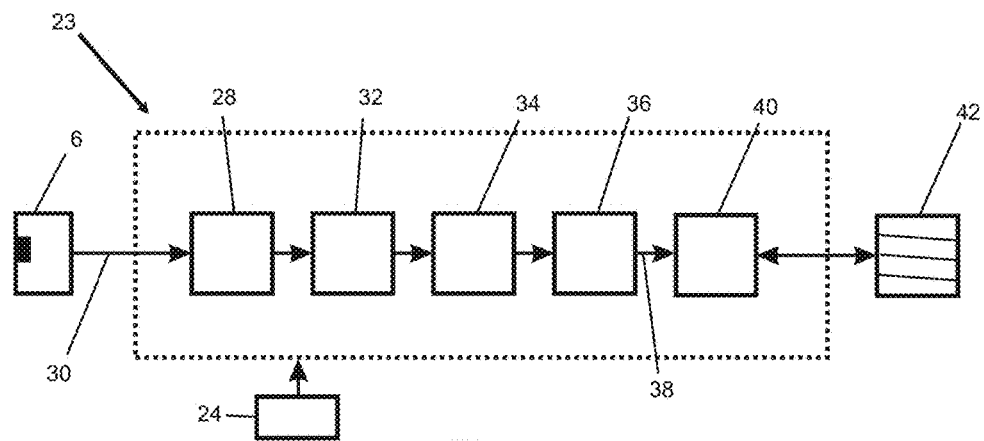
FIG. 7 shows a block diagram of an embodiment of the earplug electronics from FIGS. 4 through 6.

FIG. 7 shows a block diagram of an embodiment of the earplug electronics 23 and other earplug components from FIGS. 4 through 6. A battery 24 provides electrical power for earplug 16 components in this embodiment.

The earplug microphone 6 is connected to a microphone bias circuit 28 which provides power to the microphone 6 and processes the microphone audio signal 30. The microphone bias circuit 28 is connected to an equalization circuit 32 which can provide filtering, such as A-weighted filtering, known in the art and used in noise dosimeters. A specification for an A-weighted filter can be found in ANSI S1.42 Design Response of Weighting Networks for Acoustical Measurements, table 2.

The output of the equalization circuit 32 is processed, at least by squaring and averaging, in a processing function which provides data processing for calculation of the noise dose. In FIG. 7, this is shown as a squaring circuit 34 and averaging circuit 36. However, the processing function could also be performed by a root-mean-square (RMS) circuit as will be discussed below, which provides squaring and averaging with the addition of taking the square root of the result.

In this embodiment, the noise dose is not calculated using earplug electronics. The actual noise dose, which is a more complicated calculation, is calculated remotely in the dock unit 18 or other remote device. The noise dose calculation requires more electrical power, which would require a larger battery in an earplug.

The earplug processed signal 38, from the averaging circuit 36, is input to a sensor port of an RFID chip 40. In this way, the processed signal 38 from the microphone 6 can be sampled by the RFID chip 40.

Figure 8:
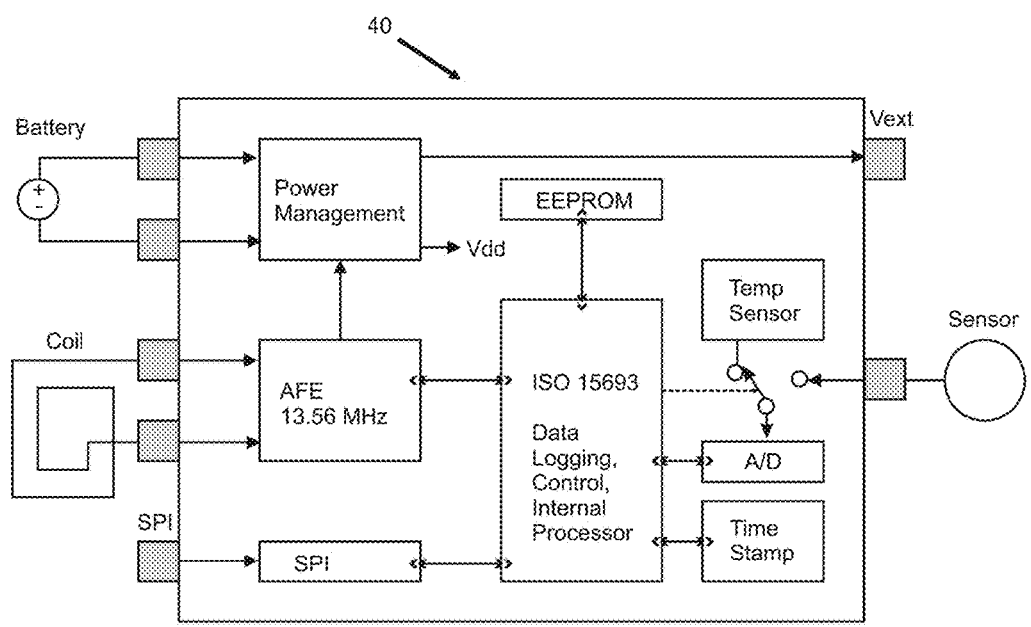
FIG. 8 shows a block diagram of a prior art RFID chip.

A schematic of an RFID chip can be seen in FIG. 8 (prior art). This RFID chip schematic was derived from the specification of a commercially available chip, the AMS SL13A RFID sensor tag and data logger IC manufactured by the Austrian company ams AG, but it will be understood that this is for example only and other chips may be used within the teaching of the invention. The chip 40 can be powered using an external battery, but can also be powered using a coil and an external magnetic field. The chip 40 has an output voltage that can be used to power external electrical components. The chip 40 may be controlled using external digital logic through an SPI controller. The chip 40 also has an external sensor input. Internally, the chip 40 has EEPROM program memory, a data logging circuit for storing data with a time stamp created by a time circuit, an analog to digital converter (A/D) with sampling capability, an internal processor and the ability to use a coil for wireless communications, among other functions. A temperature sensor is also built into this chip. The internal processor of the RFID chip 40 can be used for calculating noise dosage.

The RFID chip 40 in the earplug 16 can communicate with an RFID transceiver remotely located using an earplug antenna 42. The earplug antenna 42 from FIG. 7, in this embodiment, is the coil from FIG. 8 (prior art).

While the term "RFID chip" and "RFID transceiver" is used herein, it will be understood that this term is intended to mean a radio-frequency transmitter or transceiver circuit capable of transmitting the data from the earplug to the remote circuit or dock described below. It is not intended to limit the invention to specific chips intended solely for RFID purposes.

The noise dose can thus be determined remotely using an integrator and calculations described in ANSI S1.25 (Specification for Noise Dosimeters), for example. This has significant benefits because the noise dose calculation requires additional electrical power. This novel process of splitting the noise dose calculation into two separated calculations in two separate physical systems, one done in the earplug and one outside of the earplug, enables the use of a smaller battery in the earplug, which means a smaller, better-fitting and more comfortable earplug can be employed in this embodiment. This is important because earplugs need to be very small so they can fit comfortably in the ear.

In this embodiment, the filtered, squared and averaged earplug microphone data are exported to another device that calculates the noise dose using an integrator. The earplug processing may also contain a square root circuit so that filtered root mean squared data are exported. The external device can be a smart phone or other handheld device that can be used to spot check the user's noise dose. The device only needs to be held in the vicinity of the earplug in question. The data are then downloaded and the noise dose is calculated in the remote device. In other embodiments of the invention, the RFID chip or a separate chip within the earplug 16 calculates the noise dose.

There are some electronic chips, such as "all-in-one" digital audio processing chips, that can provide the microphone bias, equalization, squaring and averaging functions in one single chip if programmed properly. An earplug microphone may be connected directly to an "all-in-one" audio chip and its output, in digital or analog form, may be directly connected to an RFID chip. However, these "all-in-one" chips typically require more electrical power compared to analog solutions and typically require a larger battery.

Figure 9:
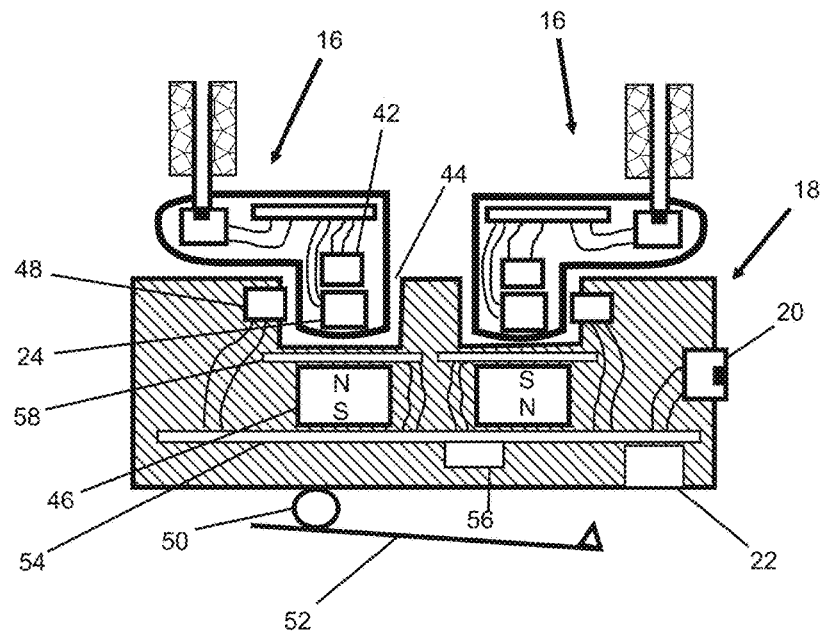
FIG. 9 shows a cross section of the embodiment of a dock unit from FIG. 4.

A cross section of the embodiment of a dock unit 18 from FIG. 4 of the current invention is shown in FIG. 9. The dock unit has several novel features. The dock unit has recesses 44 that the earplugs 16 can fit into for storage. To secure the earplugs 16 in place in this embodiment, dock magnets 46 are used to create a retention force due to attraction to components in the earplugs 16, such as the earplug battery 24. The dock unit 18 has switches 48 that are activated when the earplugs 16 are stored in the dock unit 18.

The dock unit 18 in this embodiment includes a spring 50 and clothes clip 52 that can be used to attach the dock unit 18 to the user's clothing, preferably at the shoulder location. Another convenient location to clip the dock unit 18 would be to a shirt pocket. An ambient microphone 20 mounted to the dock unit 18 is used to monitor ambient sound. A vibration transducer 22 in the dock unit 18 can be used to alert the user of events such as reaching maximum noise dose.

The switches 48, ambient microphone 20 and vibration transducer 22 communicate with dock unit electronics 54. A battery 56 provides power for dock unit electronics 54.

Dock unit transceiver antennas 58 are used to communicate with the transceiver antennas 42 of each earplug 16. Magnetic fields are used in this embodiment for wireless communications.

Processed earplug microphone data may be communicated to dock unit electronics 54 for further processing. For example, the earplug microphone signal 38 that has been equalized, squared and averaged may be downloaded to the dock unit 18 where these data are used to calculate noise dosage using an integrator and other processors. The wireless magnetic communication between the dock unit transceiver antennas 58 and earplugs 16 may also be used to recharge the earplug batteries 24.

A dock unit 18 may be used for each earplug 16 and worn on each shoulder. The dock unit 18 may also be attached to items such as hard hats. LED lights may be used on the dock unit 18 to indicate when the earplugs 16 are docked and not docked. This would be useful for a supervisor in quickly determining if the earplugs 16 are being worn, as a red LED is easily seen at a distance.

Figure 10:
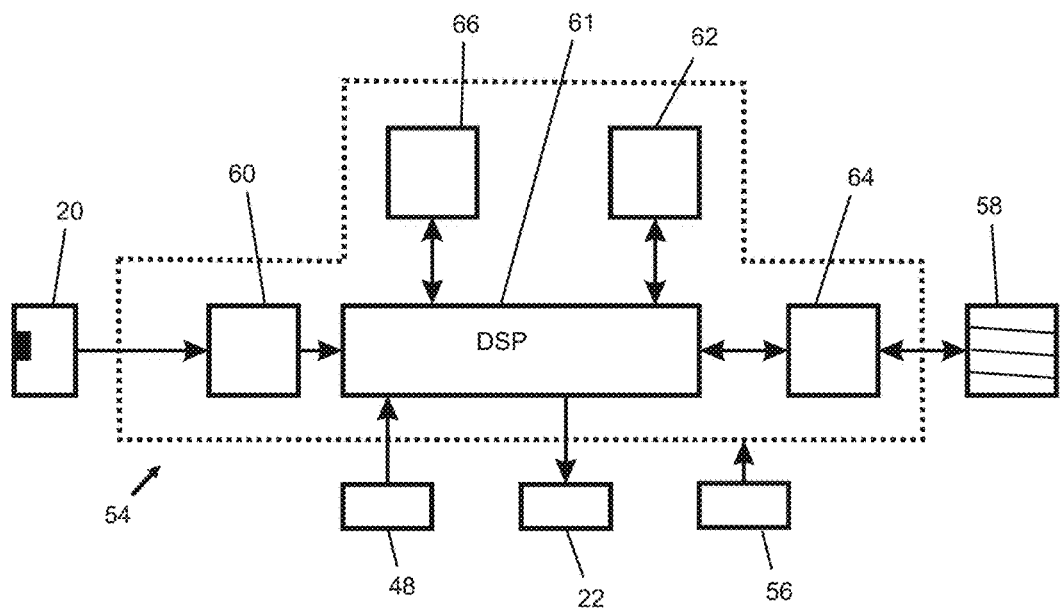
FIG. 10 shows a block diagram of the dock unit electronics and other dock unit components.

FIG. 10 is a block diagram of the dock unit 18 electronics 54 and other dock unit 18 components. The ambient microphone 20 constantly monitors the noise level at the dock unit location, on the user's shoulder in the preferred embodiment. A microphone bias circuit 60 provides power and filtering to the ambient microphone output signal, and the microphone bias signal is input to a digital signal processor (DSP) 61, in this preferred embodiment. The DSP 61 calculates the noise dose at the ambient microphone 20 location. Data may be stored in a memory chip 62. The DSP 61 can communicate to other devices, including the earplugs 16, using an RFID chip 64 and dock unit transceiver antenna 58.

At least one switch 48, in this embodiment, is used to detect when an earplug 16 is stored in the dock unit 18. This information is important because the dock unit 18 can time stamp when the user's ear is unprotected. A switch 48 for each earplug 16 is preferred. The dock unit electronics 54 can communicate with a vibration transducer 22 to alert the user of various problems, such as high noise dose. The filtered, squared and averaged data are downloaded from the earplugs 16 using the dock unit transceiver antennas 58. An integrator 66 is used to calculate the noise dose from each earplug 16. The integrator 66 may be incorporated within the DSP 61 or may be a separate circuit.

Figure 11:
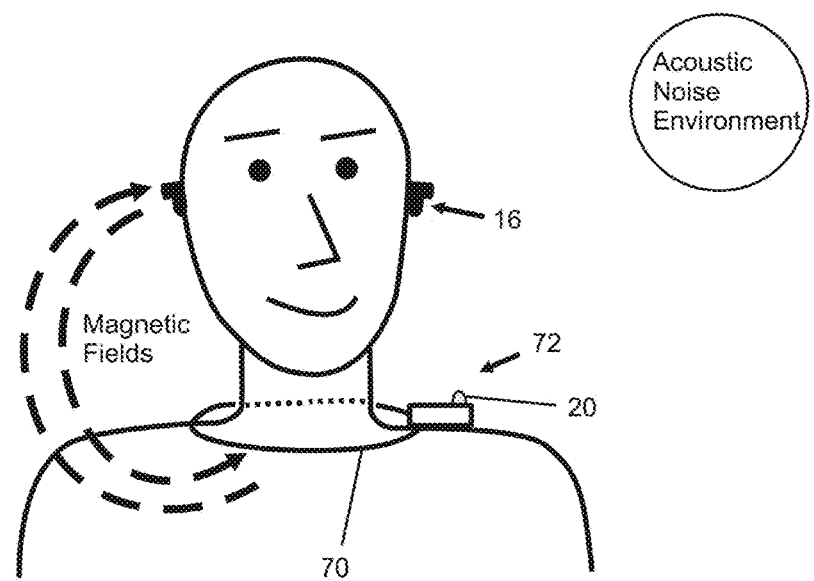
FIG. 11 shows an in-ear dosimetry system employing a neckloop as a transceiver antenna.

FIG. 11 shows an in-ear dosimetry system employing a neckloop 70 as a transceiver antenna. The neckloop 70 consists of at least one turn of electrical wire. A dock unit 72 in this embodiment communicates with the earplugs 16, wirelessly, using the neckloop 70 by generating magnetic fields. (The figure shows magnetic fields for only one of two channels to improve clarity.) The dock unit 72 is clipped to the clothing of the user, in this embodiment, so that the dock unit 72 rests on the shoulder. The neckloop 70 may also be worn like a necklace with the dock unit 72 hanging against the chest or other locations in other embodiments.

Figure 12:
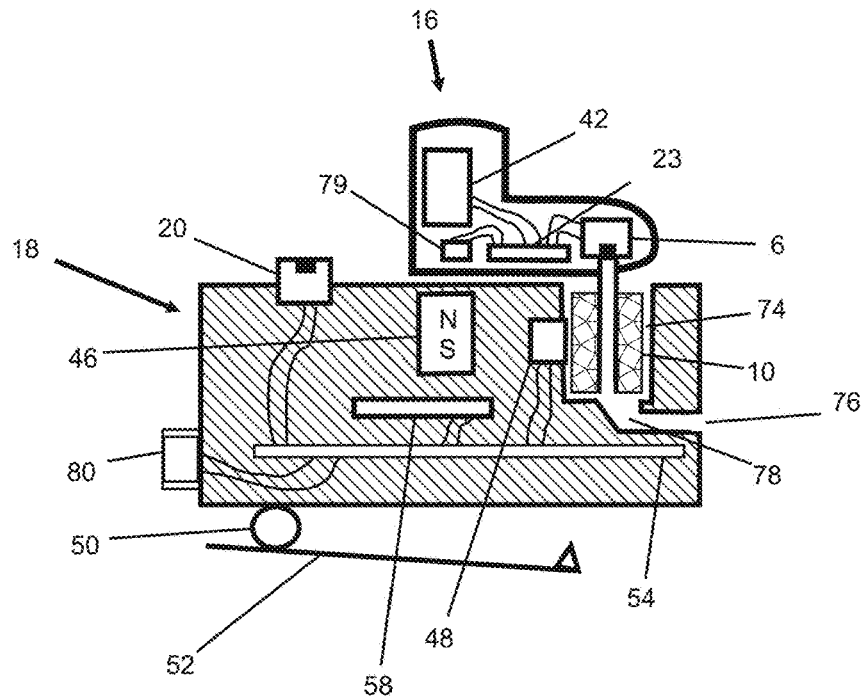
FIG. 12 shows a cross section of an earplug and dock unit for this embodiment.

The cross section of an earplug 16 and dock unit 18 for this embodiment can be seen in FIG. 12. Note that only one earplug 16 is shown, for clarity, but a second earplug can be stored in the dock unit 18 in a similar way. In this embodiment, the earplug 16 is stored with the majority of the eartip 10 housed within cavity 74 in the dock unit 18. The cavity 74 is acoustically coupled to the acoustic noise environment through an acoustic port 76 and an acoustic network 78 that may consist of tubes, chambers, screens and other acoustical elements.

In this embodiment, when the earplug 16 is stored in the dock unit 18, the earplug microphone 6 is acoustically coupled to the acoustic noise environment. The acoustical network 78 can be used to tailor the response of the earplug microphone 6 output when docked to compensate for a change in acoustic response in the dock unit 18 compared to the acoustic response in an ear canal 14.

The dock unit 18 of the preferred embodiment provides a hygienic place to store the earplugs 16, instead of a pants pocket, for example that could soil an eartip 10. The eartip 10 remains clean when stored in the dock units 18, and the earplugs 16 are easily accessible. Moreover, the eartips 10 are out of view, so that co-workers do not see the ear wax deposits of another co-worker, and this creates an aesthetically pleasing situation and prevents embarrassment.

In this embodiment, a proximity switch 79 is incorporated into the earplug 16 and switches state when in the presence of the magnetic field from dock magnet 46. The dock magnet 46 holds the earplug 16 in the dock unit 18. In this way, when the earplug 16 is stored in the dock unit 18 the earplug electronics 23 can be alerted by the proximity switch 79. In this way, a time stamp may be used, within the earplug electronics 23, to keep track of when the earplug 16 is stored in the dock unit 18. This indicates an unprotected ear.

A neckloop connector 80 serves to connect the neckloop 70 to the dock unit 18 electronics 54. If the neckloop 70 were to catch on an object, the connector 80 would release as a safety precaution. If the dock unit 18 becomes unclipped from the user's clothing, the neckloop 70 will prevent the dock unit 18 from falling to the floor. The dock unit 18 may also incorporate a transceiver antenna 58 that can be used to communicate with the earplugs 16 for battery charging purposes, for example, and may also include an ambient microphone 20 as was explained in other embodiments, above.

Figure 13:
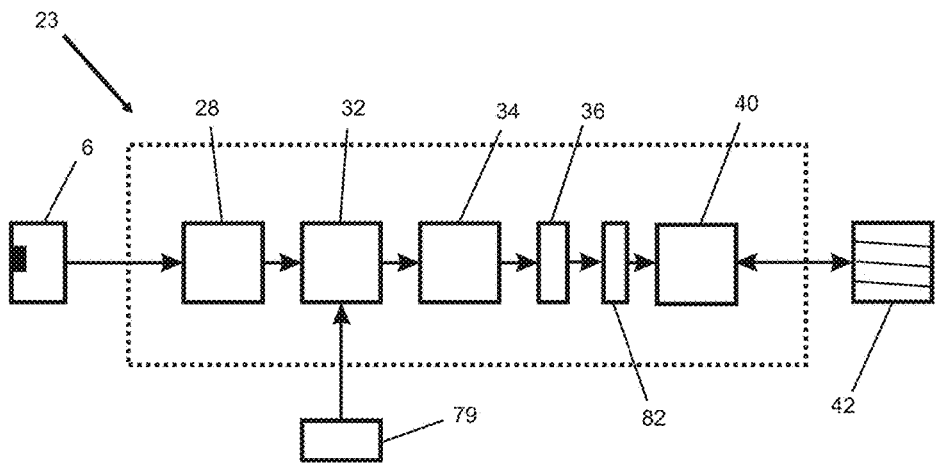
FIG. 13 shows a block diagram of the earplugs from FIG. 11.

FIG. 13 shows a block diagram of the earplug 16 electronics 23 and other components from FIG. 11. This block diagram includes the proximity switch 79 from FIG. 12. No battery is used in this embodiment because electrical power is provided wirelessly using an earplug antenna 42. In this embodiment, a square root circuit 82 is incorporated in the signal path between averaging circuit 36 and the sensor input of the RFID chip 40. The square root function 82 may be incorporated in the earplug electronics 23 or the dock unit electronics 54 and is used in calculating the noise dose. The RFID chip 40 incorporates an analog to digital converter, but a separate dedicated converter may be employed.

Figure 14:
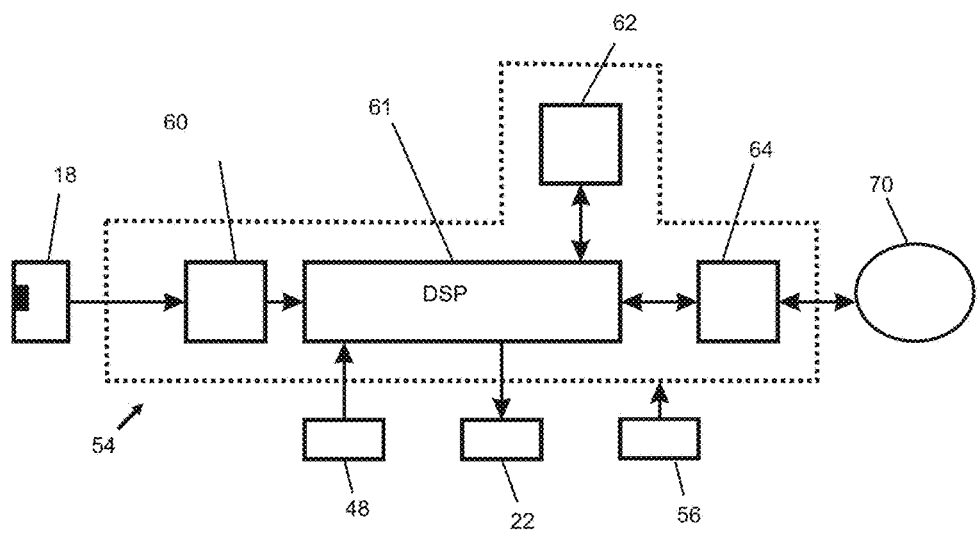
FIG. 14 shows a block diagram of the dock unit electronics and other components from FIG. 12.

FIG. 14 shows a block diagram of the dock unit 18 electronics 54 and other components from FIG. 12. This embodiment shows components shown in FIG. 10, as well as new components. A neckloop 70 is now used as the dock unit transceiver antenna. Magnetic fields produced by the neckloop 70 provide communications with the earplug 16 transceiver antenna 42 and earplug RFID chip 40 and provide wireless power for the earplug 16 electronics 23. In this embodiment, the output from the square root circuit 82 is digitized by the RFID chip 40, and this data is sent to the dock unit 18 using the earplug transceiver antenna 42 and dock transceiver antenna 70. The RFID chip 64 in the dock unit 18 receives the data and sends this to the dock unit DSP 61 where the noise exposure is calculated using equation 1 from ANSI S1.25-1991:

$$D(Q) = \frac{100}{Tc} \int_0^T 10^{[(L-Lc)]/q} dt$$

Where:
D(Q)=percentage criterion exposure for exchange rate Q;
Tc=criterion sound duration=8 hours
T=measurement duration in hours;
t=time in hours;
L=SLOW (or FAST) A-weighted sound level, a function of time, when the sound level is greater than or equal to L, or equals—infinity when the A-weighted sound level is less than Lt;
Lt=threshold sound level specified by the manufacturer;
Lc=criterion sound level specified by the manufacturer;
Q=exchange rate in decibels; and
q=10 for a 3 dB exchange rate.

The noise exposure may also be calculated within the earplug 16, in another embodiment, using the capabilities of the RFID chip 40 processor or other processor chip located within the earplug 16.

Figure 15:
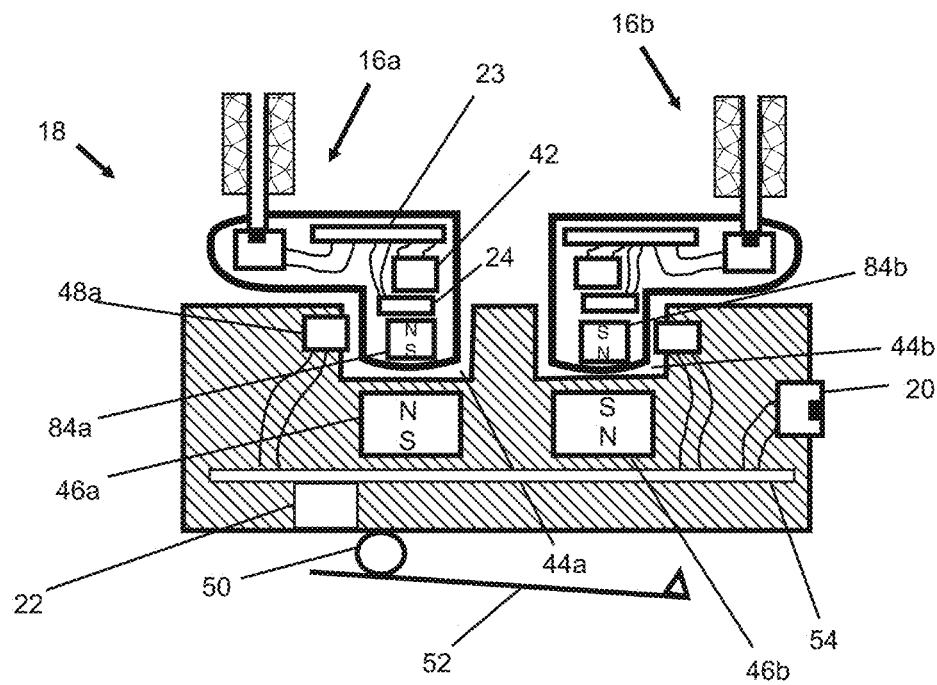
FIG. 15 shows another embodiment of a dock unit with earplugs.

FIG. 15 shows another embodiment of the invention depicting a dock unit 18 with earplugs 16. In this embodiment, dock magnets 46 and earplug magnets 84 are used that are of opposite polarity. The earplugs 16a and 16b use magnets 84a and 84b that are reversed polarity from each other. In this way, if, for example, earplug 16a is placed in the correct dock unit recess 44a, opposite polarities of the earplug magnet 84a and dock unit magnet 46a will attract, and the earplug 16a will remain secured. If an earplug 16a is placed in the incorrect recess 44b, the earplug 16a will not attach to the dock unit 18 because the magnets 84a in the earplug 16a and magnet 46b in the dock unit 18 will provide a repelling force.

Used in conjunction with dock unit switches 48, the dock unit 18 will know which earplugs 16a and 16b have been stored and which are not protecting the user's ear. The earplugs 16a and 16b are preferably color-coded or differentiated from each other in another way, for instance red for the right earplug 16b and blue for the left earplug 16a, so that the user uses a specific earplug in a specific ear at all times. In this way the dock unit 18 will know which ear is unprotected, and this information can be stored using the dock unit electronics 54.

Figure 16:
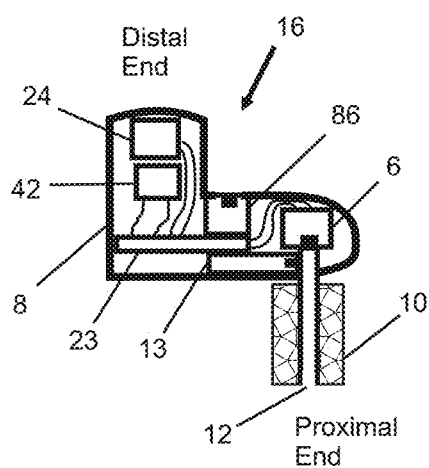
FIG. 16 shows another embodiment of the earplug of the invention.

FIG. 16 shows another embodiment of the earplug 16 of the invention. This embodiment is similar to the embodiment shown in FIG. 5a, but includes an earplug ambient microphone 86. The earplug ambient microphone 86 is acoustically coupled to the acoustic noise environment and electrically connected to the earplug electronics 23. This microphone 86 senses the unprotected noise level of the user.

An earplug canal microphone 6 is used to monitor the acoustic noise levels in the ear canal 14 when the earplug 16 is inserted in the ear 11. Comparing the data for the two microphones 6 and 86 can indicate the acoustic noise attenuation provided by the earplug 16 when worn in the ear. If the two microphones 6 and 86 indicate similar levels, this indicates that the earplug is not being worn in the ear canal.

If an additional speaker 13 is used within the earplug 16, a talk-through feature can be incorporated where the ambient microphone 86 signal is coupled to the speaker 13 and the speaker 13 is coupled to the ear canal 14 through a sound delivery channel 12. The ear canal microphone 6 would still be used for measuring noise dose exposure which would include sound levels generated by the speaker 13.

Figure 17:
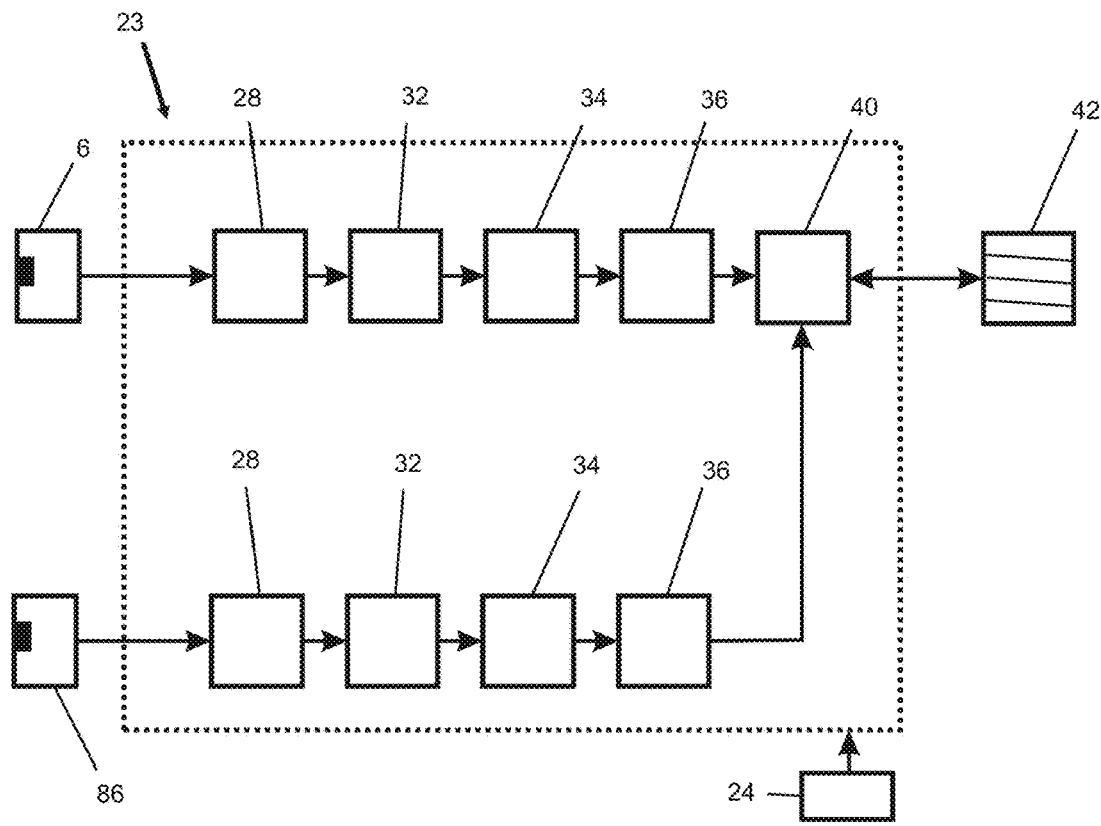
FIG. 17 shows a block diagram of a dosimeter system using the earplug of FIG. 16.

In this embodiment, as shown in FIG. 17, data from both microphones 6 and 86 are processed independently in a similar way to that shown in FIG. 7. Using two microphones 6 and 86 in the earplug 16 in this embodiment allows for useful information when noise dose levels are collected. The microphone signals are each processed by a microphone bias circuit 28, equalization circuit 32, squaring circuit 34 and averaging circuit 36, as discussed above with reference to FIG. 7. The earplug processed signal from both of the averaging circuits 36, is input to an RFID chip 40. An RMS circuit may also be used. These data are exported wirelessly for further processing using magnetic induction and an earplug antenna 42.

Figure 18:
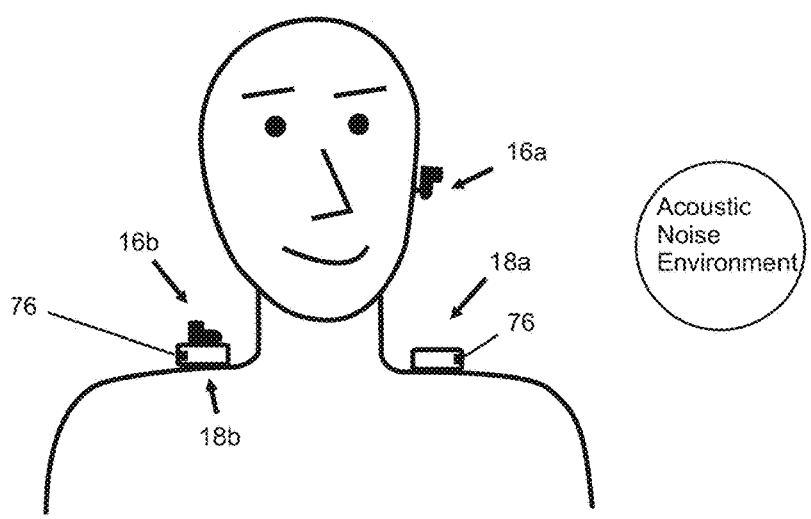
FIG. 18 shows the earplugs from FIG. 16 along with two dock units.

The earplugs 16a and 16b from FIG. 16 are shown in FIG. 18 along with two dock units 18a and 18b, secured to the user at the shoulder location using a clothes clip or other retaining device. In this embodiment, the dock units 18a and 18b are passive systems, to reduce cost. That is, there are no electronics in the dock units 18a and 18b in this embodiment. In the figure, the left earplug 16a is worn in the user's ear while the right earplug 16b is being stored in a dock unit 18b. Such a scenario might exist if the worker is having face-to-face communications with a co-worker and the worker uses one ear to hear communications while the other ear remains protected. However, both earplugs 16a and 16b may be worn in the ear, and both 16a and 16b may be stored in their respective dock units 18a and 18b, as desired.

The dock units 18a and 18b have an internal acoustic network similar to the one shown in FIG. 12 with an acoustic port 76, in this embodiment. In this way, the earplug microphones 6 monitor the noise levels at the left and right shoulder locations. Because the earplug microphones 6 monitor the unprotected noise levels at each shoulder location, compared to a single location, this configuration is more accurate compared to a single dock at a single shoulder location because each dock is closer to its respective ear, and the acoustic head shadowing problem, known in the art, is mitigated.

Figure 19:
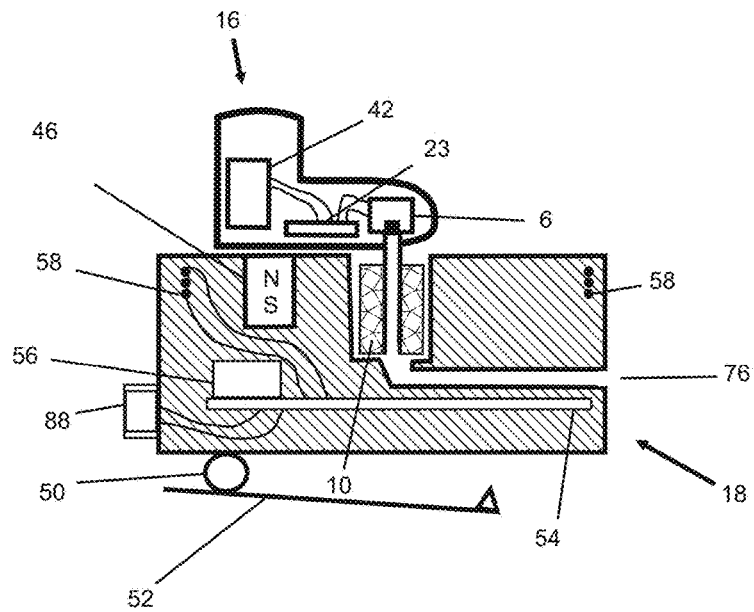
FIG. 19 shows a cross-sectional view of another embodiment of an earplug and dock unit of the invention.

In another embodiment of the invention, one dock unit 18 is shown in FIG. 19 in a cross-sectional view. The dock unit 18 has at least one dock unit transceiver antenna 58 in the form of coils that can communicate with each earplug 16. In FIG. 19, the dock unit transceiver antenna 58 in this embodiment has three turns and is shown in cross section. However, coils of more or less turns may also be incorporated.

Each dock unit 18 is relatively close, within ten inches, to its respective earplug when the earplugs 16 are worn in the ear and the dock units 18 are preferably worn on the shoulder. Thus, a low power electromagnetic signal can be used for communications between the dock unit 18 and earplugs 16, and this will require less power compared to clipping the dock unit 18 to a pants pocket, for example. The earplugs 16 can incorporate batteries, or as shown in FIG. 19, they can be battery-free and harvest power generated by dock unit transceiver antennas 58 in the dock units 18.

The dock unit 18 in this embodiment would have an overall shape like a hockey puck, but smaller in size, where the dock unit transceiver antenna coil 58 is located at the outer perimeter of the dock unit 18 for maximum transceiver antenna loop radius. Other dock unit geometries would also work, such as rectangular. A magnet 46 holds the earplug to the dock unit 18. The earplug microphone 6 is acoustically coupled to the ambient noise environment through an acoustic port 76.

Figure 20:
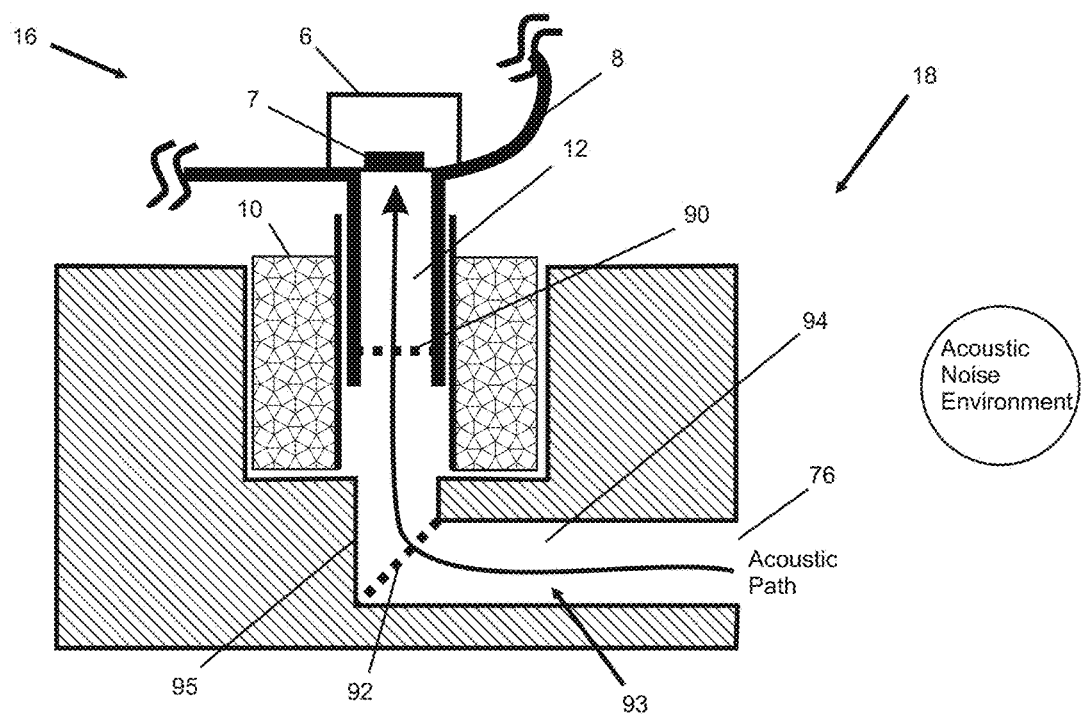
FIG. 20 shows a cross section of a passive dock unit in that it incorporates no active electronics.

Another embodiment of the invention is shown in FIG. 20. The figure depicts a cross section of a passive dock unit 18 which incorporates no active electronics. Details, such as a clothes clip for attaching the dock unit to clothes, are not included in the drawing for clarity. When the eartip 10 of the earplug 16 is inserted into the dock unit 18, the eartip 10 creates a least a partial acoustical seal with the dock unit 18 and an acoustic path is created from an acoustic port 76 on the dock unit 18 to the earplug microphone 6.

The dock unit 18 incorporates an acoustic compensator 93 that includes an acoustic port 76, a dock unit channel 94 and an acoustic damper 92 in this embodiment. The acoustic compensator 93 is acoustically coupled to the ambient acoustic noise environment through the acoustic port 76, and acoustically coupled to the earplug microphone 6 through the earplug sound delivery channel 12 and dock unit channel 94. Therefore, an acoustic path is created from the acoustic noise environment, through the dock unit 18, to the earplug microphone 6. The acoustic compensator 93 modifies the acoustic transfer function from the acoustic noise environment to the earplug microphone 6 by incorporating at least one acoustical element, such as a port, tube, damper, Helmholtz resonator, volume chamber, vent or other acoustical element.

The additional length of the acoustic path due to the dock unit channel 94 combined with the sound delivery channel 12 of the earplug to the microphone 6 creates a boosting of the frequency response at the microphone 6 between 2,000 Hz and 5,000 Hz to simulate the resonance and boosting of sound in an average unoccluded human ear. In a preferred embodiment, the acoustic compensator 93 amplifies the pressure at the earplug microphone 6 by at least 3 dB in the 2,000 Hz to 5,000 Hz region, compared to pressure sensed by the earplug microphone 6 when the earplug 16 is not in the dock unit 18. This amplification is considered to be significant.

An acoustic damper 90 in the dock unit 18 dampens this acoustic resonance, in this embodiment. The acoustic damper 90 is chosen so that the boost in earplug microphone response is at least 9 dB SPL but not greater than 18 dB compared to if the earplug microphone 6 were outside of the earplug and suspended with a string. A boost of between 11 dB and 16 dB at 2,500 Hz is desirable in this embodiment and mimics the response of a head-and-torso simulator (HATS) when subjected to a diffuse field.

An example of an HATS can be found in ITU-T P.58 specification: Head and Torso Simulator For Telephonometry. Another specification for an HATS is the ANSI S3.36

Specification for a Manikin for Simulated in-situ Airborne Acoustic Measurements, where Table III is relevant. The response of an HATS when subjected to a diffuse field, from the free field to the HATS eardrum microphone is the desired response from the acoustic noise environment to the earplug microphone in this embodiment. A suitable free-field response can be found in ITU-T P.58, table 3/P.58 Sound Pick-up Diffuse Field Frequency Response of HATS.

That is, it is desirable for the docked earplug acoustic response to mimic the free field response of an HATS. A 2,000 Hz to 5,000 Hz range for the boosting corresponds to boosting seen in table 3/P.58 of ITU-TP.58, while a boost level of between 9 dB and 18 dB falls within the boosting levels seen in table 3/P.58 of ITU-TP.58 for this frequency range. The free field response of a HATS specification may also be used instead of the diffuse field response in designing the dock unit acoustics.

When the earplug is placed in the dock unit, the combination of acoustic response of the earplug sound delivery channel 12 with the acoustic response of the dock unit 18 creates an acoustic response at the earplug microphone 6 that is similar to the response of a human eardrum to diffuse sounds outside of the ear. Helmholtz resonators, acoustic dampers and other acoustic elements and acoustical branches in the dock unit can also be used to shape the acoustic response, similar to an IEC711 canal simulator or Zwislocki coupler, so that when the earplug is docked the response from the acoustic noise environment to the earplug microphone simulate that of a human's ear.

One possible location in this embodiment for a side branch 95 is indicated in FIG. 20. This branch 95 could be a damped Helmhotz resonator, for example. This embodiment assumes that when the earplug is in a human ear, the earplug microphone pressure is a reasonably accurate representation of the eardrum pressure. An earplug acoustic damper 90 placed within the earplug 16 helps to achieve this by damping resonances of the earplug-canal acoustics.

In this embodiment, the earplug electronics 23 shown in FIG. 7 are incorporated in the earplug 16, where the equalization circuit 32 in this embodiment is shaped such that when the earplug 16 is stored in the dock unit 18 in FIG. 20, the combined response of the docked earplug acoustic response cascaded with the response of the equalization circuit 32 creates an A-weighted filter shape.

That is, when the earplug 16 is placed in the dock unit 18 and subjected to a diffuse white noise acoustic field, the power spectrum measured at the output of the equalization filter 32 will have the A-weighted response shape. In this way, when the earplug 16 is stored in the dock unit 18, and the dock unit 18 is hung by a string and placed in a diffuse acoustic field, the output from the equalization circuit 32 of the current invention will produce a similar or same output compared to the output of the A-weighted filter of a typical noise dosimeter with overall gain selected to be suitable for the specific circuits used.

When the earplug 16 is removed from the dock unit 18 and placed in a human ear 11, the acoustic response to the earplug microphone 6 will change due to the acoustics of the earplug sound channel 12 being coupled to an ear canal 14 instead of the dock unit acoustical circuit 93, but the equalization circuit 32 response will remain the same. In this embodiment of the invention seen in FIG. 20, an earplug acoustic damper 90 is used to dampen the resonance of the earplug sound delivery channel 12. This damper 90 controls unwanted sound amplification due to resonance.

When the earplug 16 is worn in an ear 11, the sound pressure at the earplug microphone 6 is similar to the sound pressure at the eardrum 15, except for the acoustic response due to the occluded ear canal and sound delivery channel 12. In this way, when the earplug 16 is stored in the dock unit 18 on the shoulder of a user, the response is very similar to the response of a typical noise dosimeter worn on the shoulder and will give accurate noise dose measurements.

When the earplug 16 is worn in the ear 11, the response will change and the measurement will de-emphasize the response in the 2,000 Hz to 5,000 Hz by at least 3 dB. This is desirable because noise dose measurements taken in the occluded ear canal should compensate for the change in acoustics in this way for more accurate noise dose measurements. This results in a more accurate noise dose measurement for in-ear noise dosimeters that are used to determine both the noise dose in the ear as well as outside the ear.

Figure 21:
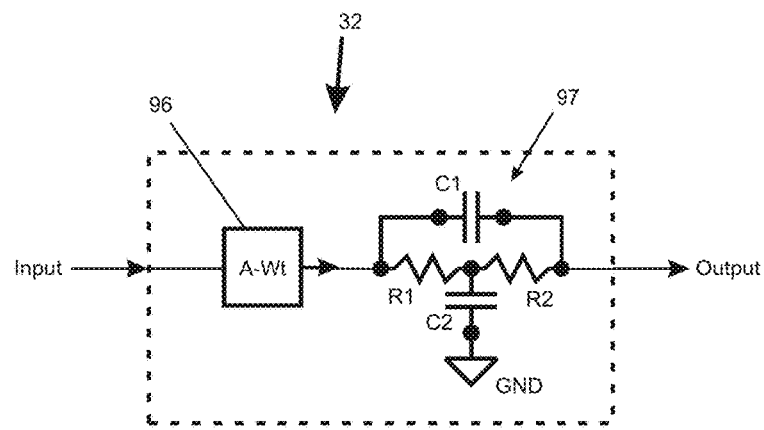
FIG. 21 shows a schematic of an A-weighted filter with a compensation filter that is a bridged-T filter.

One way to create a simple version of this novel equalization circuit 32, as shown in the embodiment of FIG. 21, is to cascade an A-weighted filter 96 with a compensation filter 97 that is a bridged-T filter. This will approximate the desired response. An electronic signal flows from the input to the A-weighted filter 96 and then to a bridged-T compensation filter 97. The bridged-T filter 97 comprises four elements in this embodiment: resistors R1 and R2 and capacitors C1 and C2.

The bridged-T filter 97 may also be implemented by including inductors and other components in the circuit. The values of R1, R2, C1 and C2 are chosen to create a notch in the 2,000 Hz to 5,000 Hz range with a dip of between 9 dB and 18 dB in this embodiment, dependent on the acoustic response achieved with the earplug 16 in the dock unit 18. More complicated versions of the bridged-T circuit 97 incorporating additional components and active amplifiers can be used for higher accuracy.

Additionally, the bridged-T filter can be integrated within the A-weighted filter 96 to create a single filter with fewer components. Values of R1=9,000 Ohm, R2=2,000 Ohm, C1=6 nF and C2=30 nF provide a dip in response of 14 dB at approximately 2,500 kHz, which is within the range of 11 dB to 16 dB at 2,500 Hz.

To the extent that when the earplug 16 is in the ear canal 14 and damped resonances affect the frequency response from the eardrum 15 to the earplug microphone 6, these effects can be compensated for with the acoustical design of the dock unit 18 and earplug equalization circuit 32.

In a preferred embodiment, the earplug equalization circuit 32 modifies the microphone 6 signal such that when the earplug 16 is in the dock unit 18 and the dock unit 18 is suspended by a string in a diffuse sound field, the power spectrum output of the equalization circuit 32 compared to the power spectrum of the diffuse sound field pressure exhibits an A-weighted curve shape. In the presence of ambient acoustic noise and the earplug 16 is in an ear 11, the output of the power spectrum of the equalization circuit 32 compared to the power spectrum of the pressure at the eardrum 15 exhibits a response curve that equals the inverse of the diffuse field response of an un-occluded ear compensated by the acoustic response of the occluded ear canal with earplug.

For example, the diffuse field response of the human ear adds 14 dB boosting to the acoustic spectrum at 2,500 Hz. If the pressure at the human ear canal is 3 dB higher when wearing the earplug compared to the pressure at the earplug microphone, 3 dB is subtracted from 14 dB to yield an earplug filter circuit response of −11 dB, instead of −14 dB for the proper design in this embodiment. This compensation technique is used at all frequencies in the preferred embodiment.

Whatever the compensation needs to be, the earplug equalization circuit 32 modifies the microphone signal 6 such that when the earplug 16 is in the dock unit 18 and the dock unit 18 is suspended by a string in a diffuse sound field, the power spectrum output of the equalization circuit 32 compared to the power spectrum of the diffuse sound field pressure exhibits an A-weighted curve shape. If a dock unit 18 is not used, the earplug equalization circuit 32 modifies the microphone 6 signal such that when the earplug 16 is suspended by a string in a diffuse sound field, the power spectrum output of the equalization circuit 32 compared to the power spectrum of the diffuse sound field pressure exhibits an A-weighted curve shape. The dock acoustics must also be modified, compared to a dock 18 unit that mimics the human ear diffuse field response, to account for occluded ear damped resonances to maintain an A-weighted response.

If the occluded ear response from eardrum 15 to earplug microphone 6 is not appreciably flat, due to a given earplug acoustic design, the designer can begin the design process by determining the proper earplug equalization circuit 32 response first. In this embodiment, the proper equalization filter 32 characteristics would be equivalent to the diffuse field unoccluded ear response compensated by the occluded ear response. This is equal to $H_{eq} = -(P_{uec}/P_a - P_{oec}/P_m)$, where $P_{uec}$ equals the unoccluded spectrum, $P_a$ is the diffuse ambient field spectrum, $P_{oec}$ is the occluded spectrum at the ear canal, $P_m$ is the occluded spectrum at the earplug microphone and $H_{eq}$ is the frequency response of the compensation filter 97, when a diffuse ambient sound field is used as a source. The transfer functions are in units of dB.

Once the $H_{eq}$ transfer function has been determined, it is combined with an A-weighted filter 96 to form the earplug equalization circuit 32 filter.

Then, the dock acoustical design must be determined. Acoustical elements, such as tubes, cavities and dampers are used to couple to the earplug sound delivery channel so that the output spectrum of the earplug equalization filter has the shape of an A-weighted filter when the earplug is in the dock unit, and the dock unit suspended by a string and placed in a diffuse sound field. Mathematically, this means that $H_a = P_{eq}/P_a$, where $H_a$ is the frequency response of an A-weighted filter and $P_{eq}$ is the spectrum at the output of the earplug equalization circuit due to a diffuse ambient pressure field of spectrum Pa.

Also, $H_a = P_m/P_a + H_{eq} + H_{eqm}$, where $H_{eqm}$ is the response of a microphone electronic filter that compensates for a microphone with non-flat inherent response to achieve a flat microphone response when the microphone is outside the earplug and suspended in free space.

In another embodiment of the invention, one can take acoustic measurements of the earplug microphone 6 in the dock unit 18, when worn on the shoulder of a HATS, to a diffuse field, and compare this result with the HATS ear canal microphone. The designer modifies the length of the dock unit channel 94 and tunes any side branches 95 in the dock unit 18 to achieve the HATS response.

Once this acoustic design has been determined, the dock unit 18 with earplug 16 is suspended by a string and subjected to a diffuse acoustic field. The response of the earplug equalization circuit 32 is then designed and modified to produce an A-weighted response when comparing the diffuse field pressure, measured with a microphone with flat diffuse field response, to the equalization circuit 32 output. This technique works well when the microphone to eardrum transfer function is relatively flat when the earplug 16 is worn in the ear 11.

In another embodiment of the invention, an acoustic response from the ambient environment to the earplug microphone 6 location when in the dock unit 18 and suspended by a string in the field is given by $H_{dua}$. The acoustic response from the ambient environment to an unoccluded human eardrum 15 (ratio of eardrum pressure over ambient pressure) is given by $H_{ua}$. The average acoustic response of the earplug microphone 6 to a human eardrum 15 (ratio of pressure at the eardrum 15 over pressure at the earplug microphone 6) when the earplug 16 is worn in the ear (occluded ear) and subjected to ambient noise is given by $H_{om}$.

The relationship between these transfer functions in the preferred embodiment is $H_{dua} = H_{ua} - H_{om}$, where the transfer functions are magnitudes and expressed in decibels. $H_{dua}$ is the target acoustic response of the earplug 16 in the dock unit 18. The designer uses acoustic elements, such as tubing, volumes, Helmhotz resonators, dampers and other acoustic elements to achieve this transfer function.

The magnitude response of $H_{dua}$ is determined by using the magnitude of the acoustic response of the human ear or suitable HATS, taken at the eardrum or simulated eardrum, subject to ambient noise. This is provided in specifications such as ITU-T P.58 or ANSI S3.36. The transfer function from input to output of an earplug compensation filter 97 is given by $H_{cf}$; $H_{ef}$ is the transfer function of an equalization circuit 32; and $H_{af}$ is the transfer function of an A-Weighted filter 96. Then $H_{ef} = H_{af} + H_{cf}$, where $H_{cf} = -H_{dua}$.

In this way, when the earplug 16 is suspended on a string and subject to ambient acoustic noise, the transfer function from the ambient noise to the output of the earplug equalization circuit 32 will look like an A-weighted filter, with appropriate scaling gain for processing the electrical signal to determine the noise dose. When the earplug 16 is worn by a user, the earplug equalization circuit 97 compensates for the unoccluded and occluded ear responses. When the earplug is placed in the dock unit 18, the dock unit acoustical elements serve to alter the acoustic response from the ambient acoustic environment to the earplug microphone 6 to compensate for the change in acoustical response of an earplug 16 in free space compared to in a human ear. The earplug compensation filter 97 has the same shape, but inverted and with appropriate overall gain, as the acoustic response of the earplug 16 in the dock unit 18.

The sum of the transfer functions $H_{dua} + H_{om}$ should preferably have a gain of between 9 dB and 18 dB, and at least 3 dB, at at least one frequency between 2,000 Hz and 5,000 Hz, when suspended from a string in a diffuse acoustic field in a preferred embodiment, based on ITU-T P.58, table 3/P.58 Sound Pick-up Diffuse Field Frequency Response of HATS. The sum of the transfer functions $H_{dua} + H_{om}$ should have a gain of between 11 dB and 16 dB, and at least 3 dB, at the third octave frequency of 2,500 Hz when the dock unit 18 is suspended from a string in a diffuse field, in another embodiment, based on ITU-T P.58, table 3/P.58 Sound Pick-up Diffuse Field Frequency Response of HATS. A gain of at least 3 dB is considered a significant change in noise dosimetry as described earlier.

Figure 22:
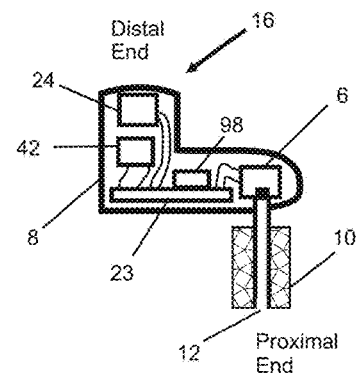
FIG. 22 shows an embodiment of an in-ear dosimeter earplug of the invention incorporating a proximity switch.

FIG. 22 shows an embodiment of an earplug 16 of the invention incorporating a switch 98. In the preferred embodiment, the switch 98 is a proximity switch and is sensitive to magnetic fields and is activated in the presence of a magnet in the dock unit 18. However, mechanical proximity switches could also be used that are activated when the earplug is placed in a dock unit 18. The earplug electronics 23 are powered using an electrical power source. In this embodiment, the electrical power source is a battery 24. However, other electrical power sources could be used, such as a charged capacitor or other device known in the art of electronics design. An earplug antenna 42 is used to communicate data collected in the earplug to a data processor remotely located (not shown). The earplug shell 8 of the earplug, in this embodiment, incorporates a microphone 6 as a sensor for measuring sound acoustically coupled from the ambient noise environment through a sound delivery channel 12. This embodiment also incorporates and eartip 10 for acoustically sealing the ear canal 14 to provide hearing protection from ambient noise.

Figure 23:
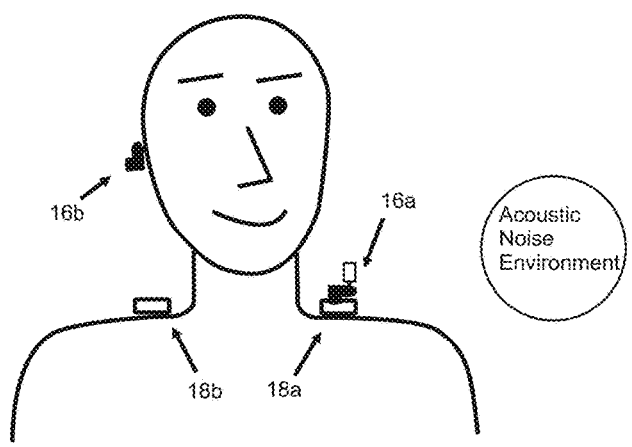
FIG. 23 shows an embodiment of the current invention with a separate dock unit for each earplug that can be worn on the shoulders for storing earplugs.

In a preferred embodiment of the invention, shown in FIG. 23, each left and right earplug 16a and 16b can be stored in its own dock unit 18a and 18b. In this preferred embodiment, the dock units 18a and 18b are small and can be clipped to the user's clothing at the preferred location on the shoulder. This can be achieved by using a clothes clip attached to each dock 18a and 18b which clips to the collar of a shirt, as shown in FIG. 23. The shoulder location is preferred because that location is close to the ear of the user. With two dock units 18a and 18b, each earplug 16a and 16b can be located close to its corresponding ear. In FIG. 23, only one of the earplugs, the left earplug 16a, is docked in dock 18a. The user may want to dock only one earplug 16a when engaged in face-to-face communications with a coworker. When docked on the left shoulder, the left earplug 16a microphone 6 measures the noise levels close to the left ear. In typical noise dosimeters, one microphone is used at the shoulder location. However, this is less accurate for measuring the unprotected exposure of both ears compared to using locations on each shoulder near each ear which can be achieved with the invention.

Figure 24:
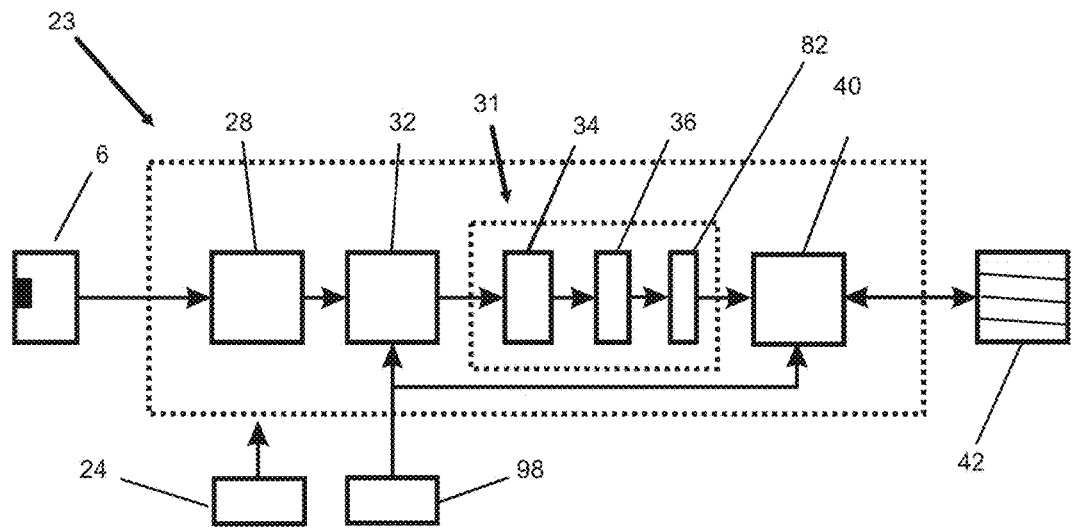
FIG. 24 shows the earplug electronics and other supporting components of the earplug embodiment from FIG. 22.

FIG. 24 shows the preferred embodiment of the earplug electronics 23 and other supporting components of the earplug 16. The earplug electronics 23 are similar to those shown in FIG. 13, except that a battery 24 is used as a power source instead of harvesting a magnetic field using the earplug antenna 42. Moreover, a different equalization circuit 32 is used and the proximity switch 98 communicates with the RFID chip 40. Similar to the embodiment shown in FIG. 13, the proximity switch 98 also communicates with the equalization circuit 32.

Figure 1:
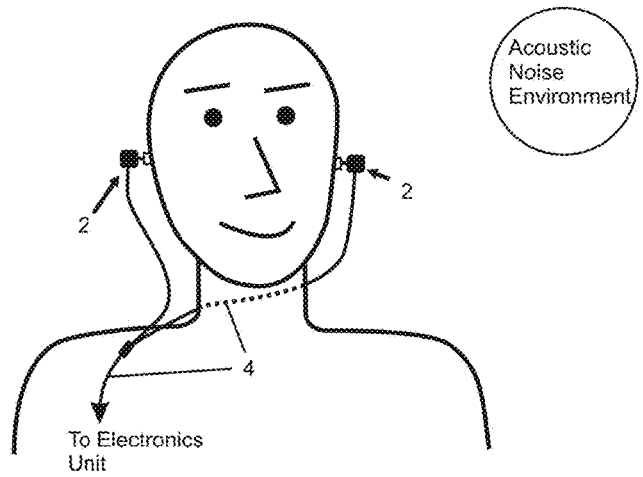
FIGS. 1-3 show prior art in-ear dosimeters.

A description of squaring and averaging, in particular, exponential averaging, a signal for noise dosimetry can be found in ANSI S1.25 (Specification for Noise Dosimeters), FIG. 1 and supporting text throughout the document. The squaring, averaging and square root circuits can be incorporated into a single chip, called an RMS detector 31, shown in FIG. 24. An example of this would be using the Linear Technology LTC1967 chip, with supporting capacitors and resistors necessary for proper operation, as seen in the LTC1967 specification. In particular, an averaging capacitor is required at the chip output. This example of an RMS circuit uses a sigma-delta converter, but other types of RMS converters are available and known in the art. Digital signal processors (DSPs) can also be used to create squaring-averaging circuits and RMS circuits.

Some squaring-averaging circuits do not directly calculate the square of a signal and then average the signal, but effectively provide the squaring and averaging function. One example would be a circuit that measures the temperature of a resistor due to a signal applied across its terminals. A positive heat measurement is recorded even if the signal across the resistor is alternating between positive and negative potential because power is dissipated in the resistor regardless of signal polarity. Averaging is achieved because of the thermal mass of the resistor. The measured temperature of the resistor can be used to determine the average squared input signal to the resistor but this technique does not require a circuit that specifically calculates the square of a signal, but effectively it can provide the squared signal average value if proper scaling of the result is used.

Exponential averaging the squared signal in noise dosimeters can yield a slowly varying electronic signal, below the audio spectrum that can be sampled at much slower sampling rates compared to sampling the squared signal, itself, or other signals in the audio spectrum. The audio spectrum is considered to be between 20 Hz and 20,000 Hz.

To properly sample a time-varying signal, the sampling rate must be greater than double the highest frequency of the signal. For an audio signal, this would be sampling at least 40,000 times per second. Signals having a spectrum below the audio spectrum can be sampled at frequencies of less than 40 (2×20) times per second.

The exponentially averaged squared signal, or RMS signal, used for a noise dose calculation can be sampled at rates of less than 40 times per second, and even once per second in some applications. Sampling the squared and exponentially averaged, or RMS, audio signal can result in 39,960 fewer samples per second in the invention due to the novel technique of sampling the averaged squared signal, or RMS signal, within the earplug instead of the audio spectrum signal derived from the microphone, which results in significant power savings.

This is critical because minimizing the battery size results in a more comfortable earplug. Moreover, in another embodiment of the invention, this reduction of power of the invention enables the operation of the earplug using wireless power transfer because of the limited capacity of wireless power systems using small earplug antennas.

Figure 25:
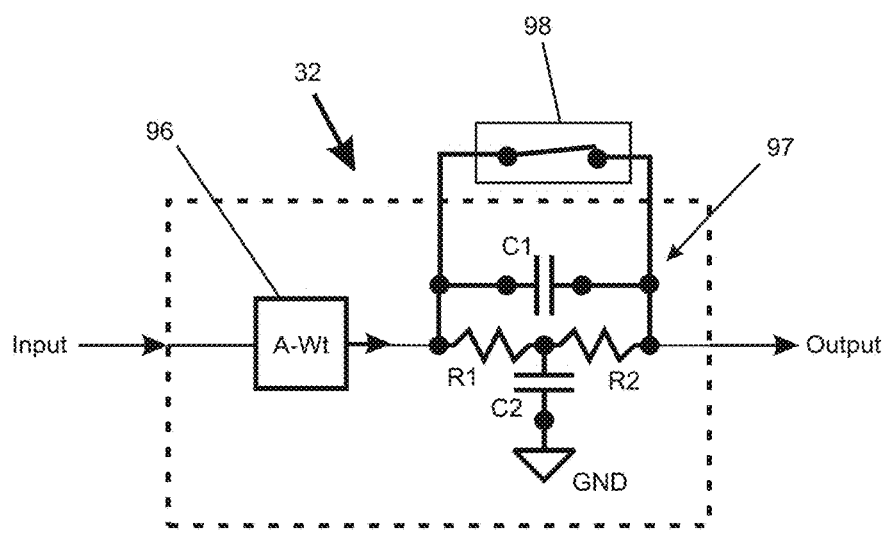
FIG. 25 shows an embodiment of equalization circuit from FIG. 24.

FIG. 25 shows details of the equalization circuit 32 shown in the embodiment of FIG. 24. This equalization circuit 32 is similar to the circuit shown in FIG. 21, except that the location of a proximity switch 98 is shown for this embodiment. The proximity switch 98 is activated when the earplug is placed in a magnetic field, for example, near a magnet in a dock unit 18. In this way, two equalization circuit responses are achieved depending on the state of the switch, and the state of the switch depends on whether the earplug 16 is in the dock 18 or not in the dock 18. The equalization circuits 32 can be analog, as shown in FIG. 25, or can be digital. In a preferred embodiment, there is at least a 3 dB difference in the response of the two filters at at least one frequency between 2 kHz and 5 kHz.

Figure 26:
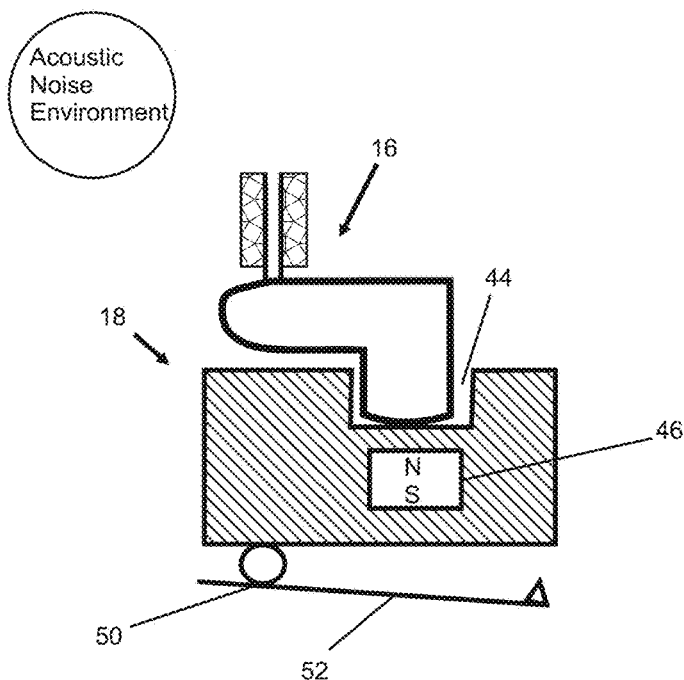
FIG. 26 shows the earplug embodiment from FIG. 22 in the dock unit from FIG. 23.

A single dock unit 18 from FIG. 23 is shown in FIG. 26. In this embodiment of the invention, the dock unit 18 is passive, in that it does not require electrical power to function and can therefore be made very inexpensively, small in size and doesn't require a battery. The interior of the earplug 16 is not shown in FIG. 26 for simplicity and clarity. This dock unit 18 incorporates a magnet 46 to hold the earplug 16 in place, due to magnetic attraction to a battery in the earplug (not shown), and to activate the proximity switch 98 within the earplug 16.

In the preferred embodiment, the proximity 98 switch modifies the compensation filter 97 frequency response. The proximity switch 98 is in the open circuit state when activated in this embodiment. This occurs when the earplug is in the dock unit, and the compensation filter 97 functions to filter the output of the A-weight filter 96. When the earplug 16 is removed from the dock 18, the proximity switch 98 is no longer in a magnetic field and the switch 98 is deactivated and in the short circuit state, and the compensation filter 97 is bypassed in the equalization circuit 32.

In this way, the earplug 16 can have two equalization settings: one when the earplug 16 is in a dock 18 and another when it isn't, such as when it is in the ear.

In this embodiment, the proximity switch 98 also communicates with the RFID chip 40 to communicate to the RFID chip 40 that the earplug 16 is in the presence of a magnetic field, such as when it is docked. The RFID chip 40 can time stamp this data to indicate when the earplug 16 is in the dock 18 and when it isn't. The RFID chip 40 also time stamps the digitized output of the square root circuit 82.

In this preferred embodiment, when the earplug is suspended from a string, with no rigid structures in close proximity that would significantly influence the acoustic response, and subject to ambient acoustic noise and a magnetic field, the transfer function from the ambient noise to the output of the earplug equalization circuit 32 will have the relative response of an A-weighting filter 96, with appropriate gain for processing the electrical signal.

When the earplug is in the ear 11, the compensation filter 98 is bypassed and a second response chosen by the designer can be achieved. The response of the microphone 6 when the earplug 16 is in the ear 11 can compensate for changes in the ear canal 14 acoustics due to a blocked canal, when the earplug 16 is worn in the ear 11, compared to an unblocked canal, when the earplug 16 is not worn, for example.

There may be additional filtering between the A-weighted filter 96 and the compensation filter 97 or prior to the A-weighted filter 96 or in other locations as determined by the designer for such purposes, for example, of equalizing the microphone 6 response. The microphone 6 output may be coupled directly through the microphone bias circuit 28 to the equalization circuit 32, or the microphone 6 output may be coupled through additional circuits to the equalization circuit 32, through for example, additional filters. In this embodiment of the invention, when the earplug 16 is subject to diffuse ambient acoustic noise and a magnetic field of sufficient strength to activate the proximity switch 98, the transfer function from the ambient noise to the input of the squaring circuit 34 will have the relative response of an A-weighting filter.

A transfer function that has the relative response, or shape, of an A-weighting filter has a sensitivity at each frequency, relative to the sensitivity of the transfer function at 1,000 Hz, such as the one shown in ANSI S1.42 (Design Response of Weighting Networks for Acoustical Measurements, Tables 1 and 2) within acceptable tolerances. The appropriate A-weighting filter depends on the standards used by a particular country or jurisdiction and may be referred to as a "target response" or other name. Another example of a target response, depending on the intended application of the invention, could be the relative response of a C-weighting filter, where the C-weighting filter characteristics can be found in ANSI 1.42.

An example of an acceptable tolerance of the target response would be the tolerance specified by a standards committee concerning noise dosimeters, such as ANSI S1.25 (Specification for Noise Dosimeters, Table 1), or other reputable standard concerning noise dosimetry relevant to the country or jurisdiction the invention is to be used. Other target responses, other than the A-weighted relative response, may be specified in different countries. Moreover, the specified A-weighting response in ANSI S1.42 and tolerances in ANSI S1.25 may be modified in the future or new standards may be issued that supersede these standards.

The target response, in the preferred embodiment of the invention, is the target transfer function, or frequency characteristics, measured from the acoustic noise environment to the input of the squaring or other non-linear processing circuitry specified for a noise dosimeter in a reputable standard that governs noise dosimetry for a given country or jurisdiction. For the United States, at this time, a target response of the preferred embodiment is the A-weighting response and tolerances specified in section 4.2 and Table 1 of ANSI S1.25. Another target response of another preferred embodiment would be the C-weighting response and tolerances specified in section 4.2 and Table 1 of ANSI S1.25.

ANSI Specifications S1.25 and S1.42 are incorporated herein by reference.

Figure 27:
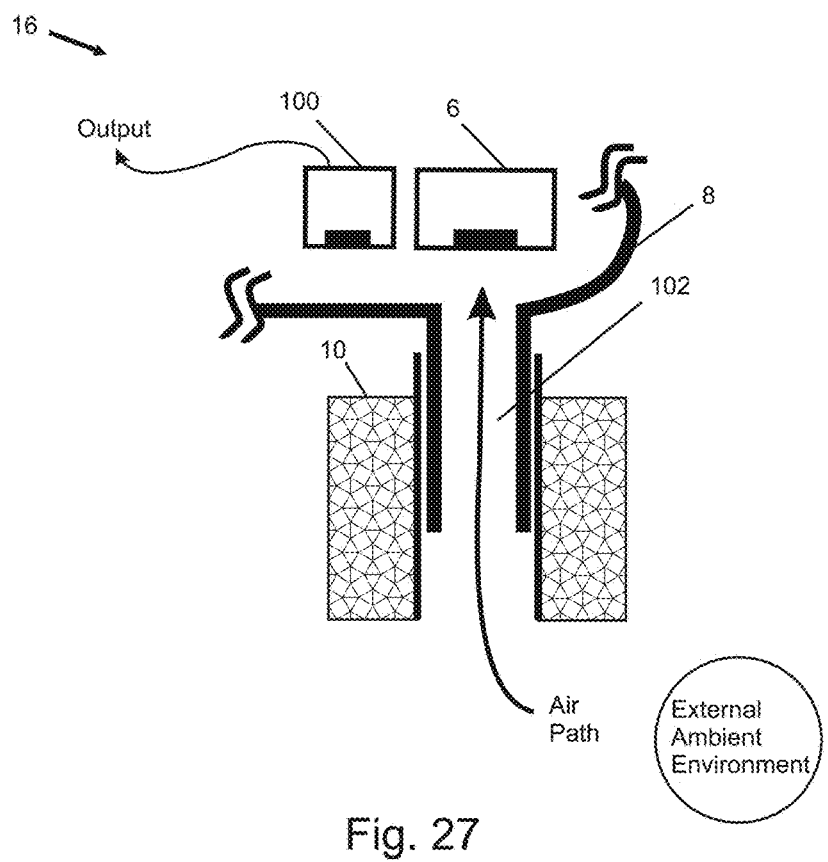
FIG. 27 shows the earplug incorporating an additional temperature sensor for sensing temperatures of the external ambient environment.

FIG. 27 shows another embodiment of the invention where the earplug 16 houses a temperature sensor 100 in addition to the earplug microphone 6. In this embodiment, the temperature sensor 100 is coupled to an external ambient environment via an air path, provided by a channel 102 through an eartip 10. The external environment is a human ear canal when the earplug 16 is worn in the ear, and is the room environment when the earplug 16 is outside of the ear.

A temperature sensor 100 output can be input to a logging circuit and other electrical circuits. When worn in the ear, the temperature sensor 100 measures the temperature of the ear canal 14, which is an indication of the human core temperature and can be used to determine if the user has a fever. The temperature sensor 100 can also be used to determine if the earplug 16 is placed in the ear canal 14 or not, when using logging, because the temperature sensor 100 will be reading two different temperatures if the room temperature is not 98.6 degrees. Typically, the temperature of the room of a work environment is below 98.6 degrees.

In this preferred environment, when the temperature sensor 100 output indicates a temperature consistent with the earplug 16 being worn in the ear, an appropriate filter is coupled to the earplug microphone 6. When the temperature sensor 100 output indicates a temperature consistent with the earplug 16 being worn outside of the ear, a second appropriate filter is coupled to the earplug microphone 6. That is, the temperature sensor 100 output is used to select one of two filter settings that are coupled to the microphone 6, similar to the way that the proximity switch 98 was used to modify the equalization circuit 32 response shown in FIG. 24 and FIG. 25. In this way, two equalization circuit responses are achieved depending on the output of the temperature sensor 100, which correspond to whether the earplug is in the ear or not in the ear.

In a preferred embodiment, there is at least a 3 dB difference in the response of the two filters at at least one frequency between 2 kHz and 5 kHz. This corresponds to a significant change in the noise exposure calculation because a 3 dB shift can enable a worker to work twice as long when using NIOSH guidelines.

Indicators are useful in dosimetry systems to alert the user when he/she is approaching overexposure limits. LEDs located on the earplugs 16 would be difficult to see, and wired indicators would be impractical.

Figure 28:
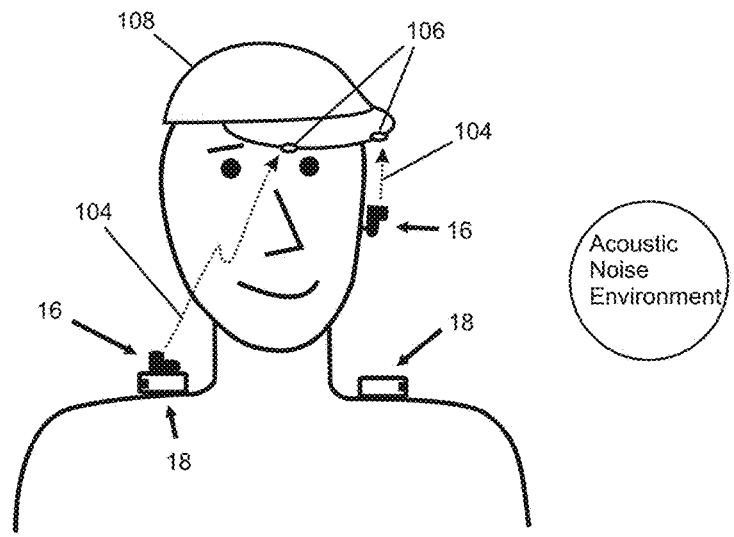
FIG. 28 shows in-ear dosimetry earplugs incorporating wireless links to remotely-located LEDs.

FIG. 28 shows another embodiment in which in-ear dosimetry earplugs 16 have wireless links 104 to remotely-located indicators 106, which could be LEDs or other light emitting devices, which can be used to alert the user when they are approaching and/or have received maximum noise dose, or other information. The indicators 106, in this embodiment, are powered using batteries and have a receiver to receive signals from the earplugs. The indicators 106 can be attached to convenient places within the line of sight of the user, such as on the brim of a hat 108 or attached to a piece of equipment that the user operates.

Figure 29:
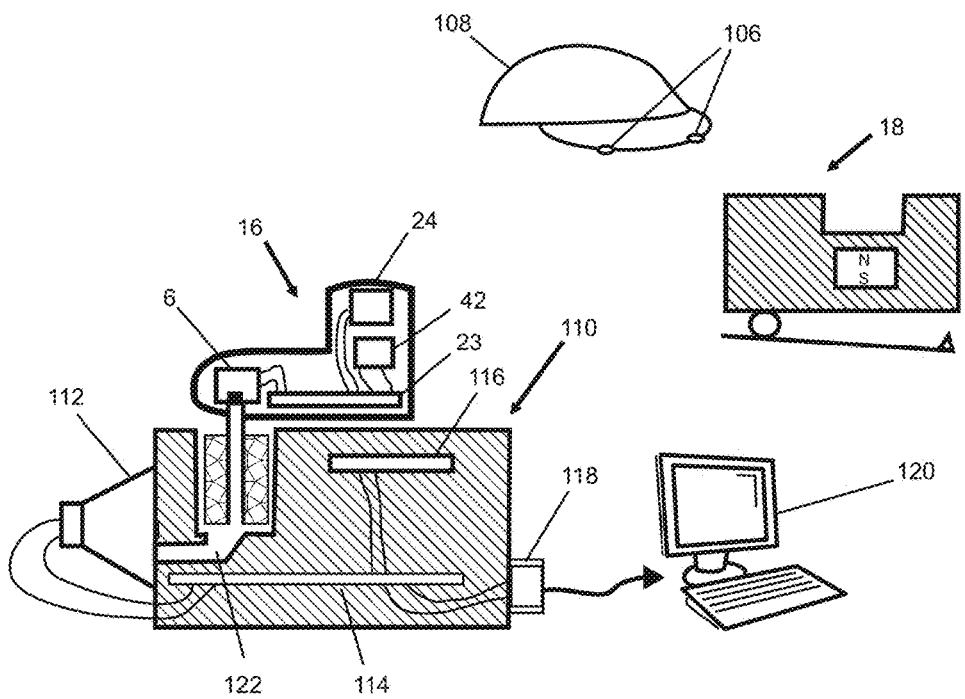
FIG. 29 shows a noise dosimetry system incorporating a noise dosimetry earplug, an earplug reader unit, a dock unit, remotely-located indicators and a computer.

FIG. 29 shows an embodiment of the noise dosimetry system incorporating a noise dosimetry earplug 16, a dock unit 18, remotely-located indicators 16 attached to a hat 108, an earplug reader unit 110 and a computer 120. In this embodiment, an earplug is placed in the reader unit 110 for the purposes of storing the earplug, calibrating the microphone 6 and earplug electronics 23, recharging the earplug battery 24 and downloading data from the earplug 16. A reader transceiver antenna 116 communicates with the earplug transceiver antenna 42 for charging the battery 24 and downloading data. An acoustic transducer, such as a speaker 112 in this embodiment, is used to generate signals for calibrating the earplug 16. The acoustic signal generated by the speaker 112 is acoustically coupled to the microphone 6 of the earplug 16 through a reader sound duct 122. Reader electronics 114 are connected to the speaker 112 and reader transceiver antenna 116. The reader electronics 114 communicate with a computer 120 via a connector 118 on the reader 110. The computer 120, in this embodiment, is used to control the functions of the reader 110 and to store downloaded data from the earplug 16.

In another embodiment of the invention, the dock 18 can hold two earplugs 16 and can be clipped to a shirt pocket or other location on a user's clothing. The dock 18 may also be attached to a hat or suspended from a necklace.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An in-ear noise dosimetry system, comprising:
   an earplug comprising:
   an eartip for insertion into a human ear canal, having a proximal end closest to an eardrum when the eartip is inserted in the ear canal, a distal end, and a sound delivery channel leading from the proximal end to the distal end;
   a microphone, acoustically coupled to the sound delivery channel at the distal end of the eartip, having a microphone electrical output;
   a processing function comprising at least averaging, having an input coupled to the microphone electrical output and an output;
   a data logging circuit, a memory, and a time circuit for creating time-indicating data; and
   a switch configured to change state between at least a first state and a second state, the time-indicating data being logged in the memory by the data logging circuit indicating when the switch changes state.

2. The noise dosimetry system of claim 1, further comprising at least one equalization circuit having an input coupled to the microphone electrical output and an output coupled to the processing function input.

3. The noise dosimetry system of claim 2, wherein the switch is coupled to the at least one equalization circuit.

4. The noise dosimetry system of claim 3, in which the switch causes the at least one equalization circuit to exhibit a first response when the switch is activated and exhibit a second response when the switch is not activated.

5. The noise dosimetry system of claim 4, wherein the first response differs from the second response by greater than 3 dB at at least one frequency between 2 kHz and 5 kHz.

6. The noise dosimetry system of claim 3, in which the switch is a magnetic field sensitive switch.

7. The noise dosimetry system of claim 3, in which the earplug further comprises a temperature sensor coupled to the switch, such that the switch is activated based on temperature sensed by the temperature sensor.

8. The noise dosimetry system of claim 2, wherein a transfer function between an ambient noise environment and the output of the at least one equalization circuits exhibits an A-weighted filter shape.

9. The noise dosimetry system of claim 1, further comprising a reader unit for downloading data from the earplug.

10. The noise dosimetry system of claim 9, in which the reader unit comprises a sound transducer for calibrating the earplug.

11. The noise dosimetry system of claim 1, in which the processing function comprises a root mean square circuit which processes a signal at the input of the processing function by squaring, averaging and taking the square root of the signal, and providing a result of the processing at the output of the processing function.

12. The noise dosimetry system of claim 1, in which the processing function comprises:
   a squaring circuit having an input coupled to the microphone electrical output and an output; and
   an averaging circuit having an input coupled to the output of the squaring circuit and an output.

13. The noise dosimetry system of claim 1, in which the earplug further comprises a digital to analog converter having an input coupled to the output of the averaging circuit, which samples at less than 40 samples per second.

14. The noise dosimetry system of claim 1, in which the earplug transceiver comprises an RFID communications system.

15. The noise dosimetry system of claim 1, in which the earplug further comprises an ambient microphone.

16. The noise dosimetry system of claim 1, further comprising a level detector for determining a noise dosage, coupled to the earplug transceiver.

17. The noise dosimetry system of claim 16, in which the noise dosimetry system further comprises at least one indicator for indicating that the noise dosage has exceeded a limit, coupled to the level detector.

18. The noise dosimetry system of claim 17, in which the at least one indicator is an LED.

19. The noise dosimetry system of claim 17, in which the at least one indicator is wirelessly coupled to the level detector.

20. The noise dosimetry system of claim 1, further comprising a dock unit for storing the earplug.

21. The noise dosimetry system of claim 20, wherein the dock unit comprises an acoustical network acoustically coupled to the earplug microphone when the earplug is stored in the dock unit.

22. The noise dosimetry system of claim 20, wherein the dock unit comprises at least one magnet for retaining the earplug when the earplug is stored in the dock unit.

23. The noise dosimetry system of claim 20, wherein the dock unit comprises a neckloop attached to the dock unit.

24. The noise dosimetry system of claim 20, in which the dock unit further comprises an ambient microphone.

25. The noise dosimetry system of claim 1, in which the earplug further comprises a speaker.

26. An in-ear noise dosimetry system, comprising:
   an earplug comprising:
   an eartip for insertion into a human ear canal, having a proximal end closest to an eardrum when the eartip is inserted in the ear canal, a distal end, and a sound delivery channel leading from the proximal end to the distal end;

a microphone, acoustically coupled to the sound delivery channel at the distal end of the eartip, having a microphone electrical output;

a processing function comprising at least averaging, having an input coupled to the microphone electrical output and an output;

at least one equalization circuit having an input coupled to the microphone electrical output and an output coupled to the processing function input; and a switch coupled to the at least one equalization circuit, the switch configured to change a state of activation as a result of the eartip being inserted into or removed from the ear canal, the switch causing the at least one equalization circuit to exhibit a first response when the switch is activated and exhibit a second response when the switch is not activated.

27. The noise dosimetry system of claim 26, wherein the first response differs from the second response by greater than 3 dB at at least one frequency between 2 kHz and 5 kHz.

28. The noise dosimetry system of claim 26, in which the earplug further comprises a temperature sensor coupled to the switch, such that the switch is activated based on temperature sensed by the temperature sensor.

29. An in-ear noise dosimetry system, comprising:
an earplug; and
a dock unit configured to store the earplug,
the earplug comprising:
an eartip for insertion into a human ear canal, having a proximal end closest to an eardrum when the eartip is inserted in the ear canal, a distal end, and a sound delivery channel leading from the proximal end to the distal end;

a microphone, acoustically coupled to the sound delivery channel at the distal end of the eartip, having a microphone electrical output;

a processing function comprising at least averaging, having an input coupled to the microphone electrical output and an output;

at least one equalization circuit having an input coupled to the microphone electrical output and an output coupled to the processing function input; and a switch coupled to the at least one equalization circuit, the switch configured to change a state of activation as a result of the earplug being stored in the dock unit or removed from the dock unit, the switch causing the at least one equalization circuit to exhibit a first response when the switch is activated and to exhibit a second response when the switch is not activated.

30. The noise dosimetry system of claim 29, wherein the first response differs from the second response by greater than 3 dB at least one frequency between 2 kHz and 5 kHz.

31. The noise dosimetry system of claim 29, wherein the switch is a magnetic field sensitive switch.

* * * * *